United States Patent [19]

Branca et al.

[11] Patent Number: 5,389,616

[45] Date of Patent: Feb. 14, 1995

[54] AMINO ACID DERIVATIVES

[75] Inventors: Quirico Branca, Basle, Switzerland; Werner Neidhart, Freiburg im Breisqau, Germany; Jenri Ramuz, Birsfelden; Henri Ramuz, Birsfelden; Heinz Stadler, Rheinfelden, all of Switzerland; Wolfgang Wostl, Grenzach-Wyhlen, Germany

[73] Assignee: Hoffman-LaRoche Inc., Nutley, N.J.

[21] Appl. No.: 99,028

[22] Filed: Jul. 29, 1993

Related U.S. Application Data

[62] Division of Ser. No. 872,736, Apr. 22, 1992, Pat. No. 5,256,645, which is a division of Ser. No. 318,576, Mar. 3, 1989, Pat. No. 5,134,123.

[30] Foreign Application Priority Data

| Mar. 4, 1988 [CH] Switzerland | 820 |
| Sep. 16, 1988 [CH] Switzerland | 3469 |
| Dec. 28, 1988 [CH] Switzerland | 4824 |

[51] Int. Cl.$^6$ ............................................. A61K 37/00
[52] U.S. Cl. ........................................ 514/18; 514/19; 514/616; 544/242; 546/138; 548/146; 548/215; 548/561; 548/566; 548/503; 548/364.7; 548/314.7; 548/365.7; 548/315.4; 548/375.1; 548/312.1; 548/506; 549/74; 549/491
[58] Field of Search ........................ 514/18, 19, 616; 544/242; 546/138; 548/146, 215, 566, 561, 803, 364.7, 314.7, 365.7, 315.4, 375.1, 312.4, 312.1, 315.1, 365.1; 549/74, 491

[56] References Cited

U.S. PATENT DOCUMENTS

| 4,657,931 | 4/1987 | Baran et al. | 514/18 |
| 4,680,284 | 7/1987 | Luly et al. | 514/18 |
| 5,250,517 | 10/1993 | Branca | 514/18 |

FOREIGN PATENT DOCUMENTS

| 189203 | 1/1986 | European Pat. Off. . |
| 020577 | 11/1986 | European Pat. Off. . |

OTHER PUBLICATIONS

Levy et al. Cardiovascular Research: Decades of Progress, A Decade of Promise Seience, vol. 217, pp. 121–129 Jul. 9, 1992.

O'Malley et al. Biochemistry & Pharmacology of Hypertension, Biochem, Soc. Trans. 10(3) pp. 164–165 (1982).

Luly et al. Journal, Medicinal Chemistry, vol. 31 #12 pp. 2264–2276, 1989.

Luly et al. Chemical Abstract, vol. 111:89 768n p. 15, 1989.

*Primary Examiner*—José G. Dees
*Assistant Examiner*—Deborah D. Carr
*Attorney, Agent, or Firm*—George M. Gould; George W. Johnston; Ellen Ciambrone Coletti

[57] ABSTRACT

The compounds of the formula

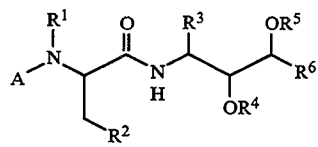

wherein A, $R^1$, $R^2$, $R^3$, $R^4$, $R^5$ and $R^6$ are as set forth above, are described.

The compounds of formula I have an inhibitory activity on the natural enzyme renin and can accordingly be used in the form of pharmaceutical preparations for the control or prevention of high blood pressure and cardiac insufficiency.

30 Claims, No Drawings

AMINO ACID DERIVATIVES

This is a division of application Ser. No. 07/872,736, filed Apr. 22, 1992, now U.S. Pat. No. 5,256,645 which is a divisional of Ser. No. 07/318,576, filed Mar. 3, 1989, now U.S. Pat. No. 5,134,123.

SUMMARY OF THE INVENTION

The invention relates to compounds of the formula

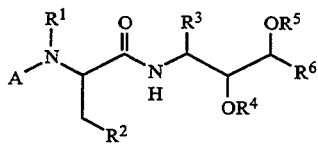

wherein $R^1$ signifies hydrogen or methyl, $R^2$ signifies ethyl, propyl, isopropyl, imidazol-2-yl, imidazol-4-yl, pyrazol-3-yl, thiazol-4-yl, thien-2-yl or t-butoxy, $R^3$ signifies isobutyl, cyclohexylmethyl or benzyl, $R^4$ and $R^5$ each independently signify hydrogen, alkanoyl, which is optionally mono- or multiply-substituted by amino, monoalkylamino, dialkylamino, alkanoylamino, alkanoyloxyamino, carboxy, alkoxy or hydroxy, or an O-protecting group or together signify a cyclic O-protecting group, $R^6$ signifies one of the groups

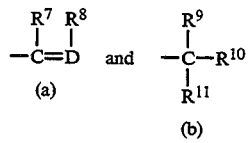

and A signifies one of the groups

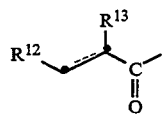

and

 (d), wherein D signifies a methyne group or a nitrogen atom, $R^7$ signifies alkyl, aryl or arylalkyl and $R^8$ signifies hydrogen, alkyl, aryl or arylalkyl or $R^7$ and $R^8$ together with the two atoms to which they are attached signify aryl, heteroaryl, cycloalkenyl or heterocycloalkenyl, $R^9$ signifies hydrogen or alkyl and $R^{10}$ and $R^{11}$ each independently signify alkyl, aryl, arylalkyl, cycloalkyl or the group

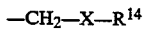

or, together with the carbon atom to which they are attached, cycloalkyl or heterocycloalkyl, with the proviso that, where $R^9$ signifies alkyl, $R^{10}$ and $R^{11}$ also signify alkyl; the dotted line can signify an additional bond, $R^{12}$ signifies phenyl, substituted phenyl, benzyl or naphthyl and $R^{13}$ signifies hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, alkoxycarbonylhydroxyalkyl, alkylcarbonylhydroxyalkyl, cycloalkylcarbonylhydroxyalkyl, heterocycloalkylcarbonylhydroxyalkyl, aryl carbonylhydroxyalkyl, aminocarbonylhydroxyalkyl, substituted aminocarbonylhydroxyalkyl, dialkoxyphosphoroxyalkyl, diphenyloxyphosphoroxyalkyl, arylalkyl, alkoxycarbonylamino, arylalkoxycarbonylamino, alkylthioalkyl, alkylsulphinylalkyl or alkylsulphonylalkyl, with the proviso that $R^{13}$ can not signify alkoxycarbonylamino or arylalkoxycarbonylamino when $R^{12}$ signifies phenyl, benzyl or α-naphthyl, Y signifies the bivalent residue of optionally N- and/or α-methylated phenylalanine, cyclohexylalanine, tyrosine, O-methyltyrosine, α-naphthylalanine or homophenylalanine linked with Z at the N-terminal, Z signifies acyl, X signifies an oxygen or sulphur atom or the group —NH— and $R^{14}$ signifies hydrogen alkyl, cycloalkyl, arylalkyl, cycloalkylalkyl, alkylcarbonyl, arylcarbonyl or arylalkylcarbonyl, in the form of optically pure diastereomers, mixtures of diastereomers, diastereomeric racemates or mixtures of diastereomeric racemates as well as pharmaceutically usable salts of these compounds. The compounds of formula I have an inhibitory activity on the natural enzyme renin and can accordingly be used in the form of pharmaceutical preparations for the control or prevention of high blood pressure and cardiac insufficiency. They can be manufactured from the corresponding, non-acylated dihydroxy derivatives and optional subsequent O-alkanoylation or conversion into O-protected derivatives.

DETAILED DESCRIPTION OF THE INVENTION

The term "alkyl" used in the present description—alone or in combination—signifies straight-chain and branched, saturated hydrocarbon residues with 1-8, preferably 1-4, carbon atoms such as methyl, ethyl, n-propyl, isopropyl, n-butyl, isobutyl, sec.-butyl, t-butyl, pentyl, hexyl and the like. The term "alkoxy" signifies alkyl ether groups in which the term "alkyl" has the above significance, such as methoxy, ethoxy, propoxy, isopropoxy, butoxy, isobutoxy, sec.-butoxy, t-butoxy and the like. The term "cycloalkyl" signifies saturated, cyclic hydrocarbon residues with 3-8, preferably 3-6, carbon atoms such as cyclopropyl, cyclobutyl, cyclopentyl, cyclohexyl and the like. The term "alkanoyl"—alone or in combination—signifies the acid residue of a straight-chain or branched alkanoic acid with 1-8, preferably 1-4, carbon atoms such as formyl, acetyl, propionyl, butyryl, valeryl, isovaleryl and the like. The term "heterocycloalkyl" relates to saturated, 3-8-membered, preferably 5- or 6-membered, cyclic hydrocarbon residues in which one or two methylene groups is/are replaced by one or two oxygen, sulphur or optionally alkyl-, phenylalkyl-, alkylcarbonyl- or alkylcarbonyloxy-substituted nitrogen atoms, such as piperidinyl, pyrazinytl, N-benzylpyrazinyl, morpholinyl, N-methylpiperidinyl, N-benzylmorpholinyl and the like. The term "cycloalkenyl" relates to an unsaturated hydrocarbon residue with 3-8; preferably 3-6, carbon atoms such as 1-cyclohexenyl, 1,4-cyclohexadienyl and the like. The term "heterocycloalkenyl" relates to the same manner to unsaturated, 3-8-membered, preferably 5- or 6-membered, cyclic hydrocarbon residues in which one or twomethylene groups is/are replaced byone or two oxygen, sulphur or optionally alkyl-, phenylakyl-, alkyl- carbonyl- or alkylcarbonyloxy-substituted nitrogen atoms, such as dihydropyranyl, dihydropyranyl, dihydropyridyl, dihydrothienyl and the like. The term "aryl" denotes a mono- or bicyclic aromatic hydrocarbon residue with 6–14 carbon atoms which is optionally mono- or multiply-substituted by alkyl, alkoxy, alkylcarbonyloxy, amino, alkylamino, dialkylamino, alkylcarbonylamino, hydroxy, halogen, trifluoromethyl or nitro, such as phenyl, α- or β-naphthyl, indenyl, anthryl or phenanthryl and the like. The term "heteroaryl" denotes an optionally partially saturated mono- or bicyclic aromatic hydrocarbon residue in which one or more carbon atoms is/are replaced by one to two nitrogen atoms and/or an oxygen or sulphur atom and which is optionally substituted on a nitrogen atom by alkyl, phenyl or phenylalkyl and/or on one or more carbon atoms by alkyl, phenyl, phenylalkyl, halogen, hydroxy, alkoxy, phenylalkoxy or oxo, such as pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benz-fused cyclopenta-, cyclohexa- or cyclohepta-fused derivative thereof, e.g. 2- or 3-pyrrolyl, phenylpyrrolyl, e.g. 4- or 5-phenyl-2-pyrrolyl, 2-furyl, 2-thienyl, 2-imidazolyl, 2-, 3- or 4-pyridyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2-indolyl, 1-benzyl-3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzthiazolyl, benz[e]indol-2-yl, β-carbolin-3-yl and the like. The term "arylalkyl" denotes straight-chain or branched alkyl groups in which one or more hydrogen atoms is/are replaced by aryl groups, such as benzyl, diphenylmethyl, trityl, α- or β-naphthylmethyl, 2-phenylethyl, 3-phenyl-2-propyl, 4-phenyl-3-butyl, 2-(α- or β-naphthyl)ethyl, 3-α-naphthyl-2-propyl, 4-α-naphthyl-3-butyl and the like, whereby the aromatic residue can in each case be mono- or multiply-substituted as indicated above. The term "substituted phenyl" denotes phenyl optionally mono- or multiply-substituted by alkyl, alkoxy, alkoxycarbonyl, alkylcarbonyloxy, hydroxy, halogen or trifluoromethyl, such as 4-hydroxyphenyl, 4-methoxyphenyl, 4-methylphenyl, 4-chlorophenyl and the like. The term "substituted amino" signifies an amino group which is mono- or di-substituted by alkyl, arylalkyl, alkylcarbonyl, alkoxycarbonyl or arylalkoxycarbonyl or disubstituted by $C_3$-$C_6$-alkylene which is optionally interrupted by an oxygen, sulphur or optionally alkyl-, phenylalkyl-, alkylcarbonyl or alkylcarbonyloxy-substituted nitrogen atom. The term "$C_3$-$C_6$-alkylene" denotes straight-chain or branched residues with 3–6 carbon atoms such as trimethylene, propylene, tetramethylene, pentamethylene, hexamethylene and the like. The term "acyl" relates to the acyl group of a carboxylic acid, an optionally N-substituted carbamic acid, a sulphonic acid or an optionally N-substituted amidosulphonic acid, especially those with the partial formulae $R^a$—CO—, $(R^a)($$R^a)$N—CO—, $R^a$—SO$_2$— or $(R^a)(R^a)$N—SO$_2$— in which $R^a$ signifies hydrogen, an unsubstituted or substituted, saturated, aliphatic, cycloaliphatic or cycloaliphatic-aliphatic hydrocarbon residue with up to 10, preferably 6, carbon atoms which is optionally functionalized with amino, monoalkylamino, dialkylamino, alkanoylamino or alkanoyloxyamino, an unsubstituted or substituted aromatic, heteroaromatic, aromatic-aliphatic or heteroaromatic-aliphatic hydrocarbon residue with up to 18, preferably 10, carbon atoms or an unsubstituted or substituted, saturated 5- or 6-membered heterocycle. The term "O-protecting group" signifies a protecting group which is cleavable with base or preferably with acid, such as the tetrahydropyranyl or methoxymethyl residue, an alkylcarbonyloxymethyl or alkoxycarbonyloxymethyl residue and the like. Examples of "cyclic O-protecting groups" are acetals and ketals such as the ketal of acetone or the acetal of pivalic aldehyde or benzaldehyde.

An unsubstituted or substituted, saturated, aliphatic, cycloaliphatic or cycloaliphatic-aliphatic hydrocarbon residue $R^a$ is, for example, unsubstituted or substituted alkyl, mono-, bi- or tricycloalkyl or cycloalkylalkyl. "Substituted alkyl" signifies an alkyl residue in which one or more hydrogen atoms can be substituted by hydroxy, alkoxy, alkylcarbonyloxy, halogen, amino or oxo, whereby the substituents are present in the 1-position of the alkyl residue only when this is present in the partial formula $R^a$—CO—.

Examples of substituted alkyl are 2-hydroxyethyl, methoxymethyl, 2-methoxyethyl, acetoxymethyl, 2-acetoxyethyl, chloromethyl, bromomethyl, 2-chloro- or 2-bromoethyl, 2-oxopropyl, 2-oxobutyl.

The term "bicycloalkyl" relates to bicyclic saturated hydrocarbon residues with 5–10, preferably 6–9, carbon atoms such as bicyclo[3.1.0]hex-1-yl, bicyclo[3.1.0]hex-2-yl, bicyclo[3.1.0]hex-3-yl, bicyclo[4.1.o]hept-1-yl, bicyclo[4.1.0]hept-4-yl, bicyclo[2.2.1]hept-2-yl, bicyclo[3.2.1]oct-2-yl, bicyclo[3.3.0]oct-3-yl, bicyclo[3.3.1]non-9-yl, α- or β-decahydronaphthyl and the like.

The term "tricycloalkyl" relates to a tricyclic saturated hydrocarbon residue with 8–10 carbon atoms such as 1-adamantyl.

Examples of cycloalkylalkyl are cyclopropylmethyl, cyclobutylmethyl, cyclopentylmethyl, cyclohexylmethyl and the like.

The aforementioned cycloaliphatic and cycloaliphatic-aliphatic residues can be substituted by the same substituents as alkyl.

An optionally substituted aromatic or aromatic-aliphatic hydrocarbon resiue is, for example, unsubstituted or substituted aryl or arylalkyl.

In a heteroaromatic or heteroarmatic-aliphatic hydrocarbon residue the heterocycle is mono-, bi- or tricyclic and contains one to two nitrogen atoms and/or one oxygen or sulphur atom and is linked with the group —CO—, >N—CO—, —SO$_2$ or >N—SO$_2$— with one of its ring carbon atoms. Examples of such heteroaromatic hydrocarbon residues are pyrrolyl, furyl, thienyl, imidazolyl, pyrazolyl, oxazolyl, thiaxolyl, pyridyl, pyrazinyl, pyrimidinyl, indolyl, quinolyl, isoquinolyl, quinoxalinyl, β-carbolinyl or a benz-fused cyclopenta-, cyclohexa- or cylohepta-fused derivative of these residues. The heteroarmatic residue can be substituted on a nitrogen atom by alkyl, phenyl or phenylalkyl, e.g. benzyl, and/or one or more carbon atoms by alkyl, phenyl, phenylalkyl, halogen, hydroxy, alkoxy, phenylalkoxy or oxo and can be partially saturated. Examples of such heteroaromatic residues are 2- or 3-pyrrolyl, phenylpyrrolyl, e.g. 4- or 5-phenyl-2-pyrrolyl, 2-furyl, 2-thienyl, 2-imidazolyl, 2-, 3- or 4-pyridyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2-indolyl, 1-benzyl-3-indolyl, 4,5,6,7-tetrahydro-2-indolyl, cyclohepta[b]-5-pyrroly, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzthiazolyl, benz[e]indol-2-yl, β-carbolin-3-yl and the like.

Examples of heteroaromatic-aliphatic hydrocarbon residues are 2- or 3-pyrrolylmethyl, 2-, 3- or 4-pyridylmethyl, 2-(2-, 3- or 4-pyridyl)ethyl, 4-imidazolylmethyl, 2-(4-imidazolyl)ethyl, 2-indolylmethyl, 3-indolylmethyl, 2-(3-indolyl)ethyl, 2-quinolylmethyl and the like.

A saturated 5- or 6-membered heterocycle has at least one carbon atom, 1–3 nitrogen atoms and optionally one oxygen or sulphur atom as the ring member(s) and is linked with the group —CO—, >N—CO—, —SO$_2$ or >N—SO$_2$- with one of its ring carbon atoms. The heterocycle can be substituted on one of its carbon atoms or on a ring nitrogen atom by alkyl, e.g. methyl or ethyl, phenyl or phenylalkyl, e.g. benzyl, or on one of its carbon atoms by hydroxy or oxo and/or can be benzfused on two adjacent carbon atoms. Examples of such heterocycles are pyrrolidin-3-yl, 4-hydroxypyrrolidin-2-yl, 5-oxo-pyrrolidin-2-yl, piperidin-2-yl, piperidin-3-yl, 1-methylpiperidin-2-yl, 1-methylpiperidin-3-yl, 1-methylpiperidin-4-yl, morpholin-2-yl, morpholin-3-yl, thiomorpholin-2-yl, thiomorpholin-3-yl, 1,4-dimethylpiperazin-2-yl, 2-indolinyl, 3-indolinyl, 1,2,3,4-tetrahydroquinol-2-, -3- or -4-yl, 1,2,3,4-tetrahydroisoquinol-1-, -3- or -4-yl, 1-oxo-1,2,3,4-tetrahydroisoquinol-3-yl and the like.

The term "pharmaceutically usable salts" embraces salts with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like. Such salts can be manufactured readily by any person skilled in the art having regard to the state of the art and taking into consideration the nature of the compound to be converted into a salt.

The invention is concerned with amino acid derivatives. In particular, it is concerned with amino acid derivatives of the formula

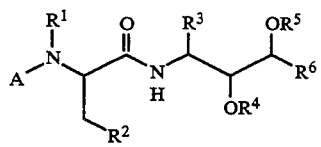

I wherein $R^1$ signifies hydrogen or methyl, $R^2$ signifies ethyl, propyl, isopropyl, imidazol-2-yl, imidazol-4-yl, pyrazol-3-yl, thiazol-4-yl, thien-2-yl or t-butoxy, $R^3$ signifies isobutyl, cyclohexylmethyl or benzyl, $R^4$ and $R^5$ each independently signify hydrogen, alkanoyl, which is optionally mono- or multiply-substituted by amino, monoalkylamino, dialkylamino, alkanoylamino, alkanoyloxyamino, carboxy, alkoxy or hydroxy, or an O-protecting group or together signify a cyclic O-protecting group, $R^6$ signifies one of the groups

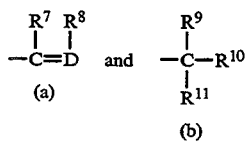

and A signifies one of the groups

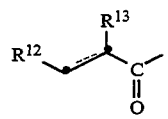

(c)

and

—Y—Z          (d), wherein D signifies a methyne group or a nitrogen atom, $R^7$ signifies alkyl, aryl or arylalkyl and $R^8$ signifies hydrogen, alkyl, aryl or arylalkyl or $R^7$ and $R^8$ together with the two atoms to which they are attached signify aryl, heteroaryl, cycloalkenyl or heterocycloalkenyl, $R^9$ signifies hydrogen or alkyl and $R^{10}$ and $R^{11}$ each independently signify alkyl, aryl, arylalkyl, cycloalkyl or the group

—CH$_2$—X—R$^{14}$          (e)

or, together with the carbon atom to which they are attached, cycloalkyl or heterocycloalkyl, with the proviso that, where $R^9$ signifies alkyl, $R^{10}$ and $R^{11}$ also signify alkyl, the dotted line can signify an additional bond, $R^{12}$ signifies phenyl, substituted phenyl, benzyl or naphthyl and $R^{13}$ signifies hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonylhydroxyalkyl, aminocarbonylhydroxyalkyl, substituted aminocarbonylhydroxyalkyl, dialkoxyphosphoroxyalkyl, diphenyloxyphosphoroxyalkyl, arylalkyl, alkoxycarbonylamino, arylalkoxycarbonylamino, alkylthioalkyl, alkylsulphinylalkyl or alkylsulphonylalkyl, with the proviso that $R^{13}$ can not signify alkoxycarbonylamino or arylalkoxycarbonylamino when $R^{12}$ signifies phenyl, benzyl or α-naphthyl, Y signifies the bivalent residue of optionally N- and/or α-methylated phenylalanine, cyclohexylalanine, tyrosine, O-methyltyrosine, α-naphthylalanine or homophenylalanine linked with Z at the N-terminal, Z signifies acyl, X signifies an oxygen or sulphur atom or the group —NH— and $R^{14}$ signifies hydrogen, alkyl, cycloalkyl, arylalkyl, cycloalkylalkyl, alkylcarbonyl, arylcarbonyl or arylalkylcarbonyl, in the form of optically pure diastereomers, mixtures of diastereomers, diastereomeric racemates or mixtures of diastereomeric racemates as well as pharmaceutically usable salts of these compounds.

These compounds are novel and are distinguished by valuable pharmacodynamic properties.

Objects of the present invention are the compounds of formula I and their pharmaceutically usable salts per se and for use as therapeutically active substances, the manufacture of these compounds, medicaments containing these compounds and the manufacture of such medicaments, as well as the use of compounds of formula I and their pharmaceutically usable salts in the control or prevention of illnesses or in the improvement of health, especially in the control or prevention of high blood pressure and cardiac insufficiency.

The compounds of formula I have at least three asymmetric carbon atoms and are therefore present in the form of optically pure diastereomers, mixtures of diastereomers, diastereomeric racemates or mixtures of diastereomeric racemates. The present invention embraces all forms. Mixtures of diastereomers, diastereomeric racemates or mixtures of diastereomeric racemates can be separated according to usual methods, e.g. by column chromatography, thin-layer chromatography, HPLC and the like.

Those compounds of formula I in which $R^1$ signifies hydrogen are preferred. $R^2$ preferably signifies imidazol-2-yl, imidazol-4-yl or thiazol-4-yl, particularly imidazol-4-yl. Further, those compounds of formula I in which $R^3$ signifies cyclohexylmethyl are preferred. Preferably, $R^4$ and $R^5$ each independently signify hydrogen or alkanoyl, which is optionally mono-substituted by methoxy, or together signify the acetal of pivalic aldehyde, especially in each case hydrogen. Also preferred are those compounds of formula I in which $R^6$ signifies the group (b). Likewise preferred are the compounds of formula I in which A signifies the group (c). The preferred significance of $R^9$ is hydrogen. Preferably, $R^{10}$ and $R^{11}$ each signify alkyl or, together with the carbon atom to which they are attached, cycloalkyl, particularly methyl, ethyl, cyclopropyl or cyclobutyl. $R^{12}$ preferably signifies phenyl or substituted phenyl, particularly phenyl. The preferred significance of $R^{13}$ is alkylcarbonylalkyl or alkylsulphonylalkyl, preferably $C_1$-$C_4$-alkylcarbonylmethyl or $C_1$-$C_4$-alkylsulphonylmethyl. Where A signifies the group (d), then there are preferred those compounds of formula I in which Y signifies the bivalent residue of phenylalanine linked with Z at the N-terminal. Z preferably signifies the group $R^a$—CO— in which $R^a$ signifies an optionally substituted, saturated aliphatic hydrocarbon residue with up to 10 carbon atoms or an optionally substituted heteroaromatic hydrocarbon residue with up to 18 carbon atoms, particularly the group $R^a$—CO— in which $R^a$ signifies a saturated, aliphatic hydrocarbon residue with up to 6 carbon atoms or a heteroaromatic residue with up to 10 carbon atoms.

From the above it follows. that there are particularly preferred those compounds of formula I in which $R^1$ signifies hydrogen, $R^2$ signifies imidazol-4-yl, $R^3$ signifies cyclohexylmethyl, $R^4$ and $R^5$ each signify hydrogen, $R^6$ signifies the group (b), $R^9$ signifies hydrogen, $R^{10}$ and $R^{11}$ each signify methyl or ethyl or, together with the carbon atom to which they are attached, cyclopropyl or cyclobutyl, $R^{12}$ signifies phenyl and $R^{13}$ signifies $C_1$-$C_4$-alkylcarbonylmethyl or $C_1$-$C_4$-alkylsulphonylmethyl.

Particular compounds of formula I are those in which $R^1$ signifies hydrogen, $R^2$ signifies propyl, imidazol--2-yl, imidazol-4-yl, thiazol-4-yl, thien-2-yl or t-butoxy, $R^3$ signifies cyclohexylmethyl, $R^4$ and $R^5$ each independently signify hydrogen or alkanoyl, which is optionally mono-substituted by dialkylamino, carboxy or alkoxy, or together signify a cyclic O-protecting group, $R^6$ signifies the group (a) or (b), A signifies the group (c) or (d), D signifies a methyne group, $R^7$ signifies alkyl and $R^8$ signifies hydrogen or alkyl or $R^7$ and $R^8$ together with the two atoms to which they are attached signify aryl, heteroaryl or cycloalkenyl, $R^9$ signifies hydrogen or alkyl, $R^{10}$ and $R^{11}$ each independently signify alkyl or the group (e) or, together with the carbon atom to which they are attached, cycloalkyl or heterocycloalkyl, $R^{12}$ signifies phenyl, substituted phenyl, benzyl or naphthyl, $R^{13}$ signifies alkylcarbonylalkyl, heterocycloalkylcarbonylalkyl, alkylcarbonylhydroxyalkyl, dialkoxyphosphoroxyalkyl, arylalkyl, alkylsulphinylalkyl or alkylsulphonylalkyl, Y signifies the bivalent residue of phenylalanine linked with Z at the N-terminal, Z signifies acyl, X signifies an oxygen atom and $R^{14}$ signifies hydrogen or arylalkyl.

Quite particular compounds of formula I are those in which $R^1$ signifies hydrogen, $R^2$ signifies imidazol-2-yl, imidazol-4-yl or thiazol-4-yl, especially imidazol-4-yl, $R^3$ signifies cyclohexylmethyl, $R^4$ and $R^5$ each independently signify hydrogen or alkanoyl, which is optionally mono-substituted by methoxy, or together signify the acetal of pivalic aldehyde, especially in each case hydrogen, $R^6$ signifies the group (b), A signifies the group (c), $R^9$ signifies hydrogen, $R^{10}$ and $R^{11}$ each independently signify alkyl or, together with the carbon atom to which they are attached, cycloalkyl, especially methyl, ethyl, cyclopropyl or cyclobutyl, $R^{12}$ signifies phenyl or substituted phenyl, especially phenyl, and $R^{13}$ signifies alkylcarbonylalkyl or alkylsulphonylalkyl, especially $C_1$-$C_4$-alkylcarbonylmethyl or $C_1$-$C_4$-alkylsulphonylmethyl.

Especially preferred compounds of formula I are:

(S)-N- [(1S, 2R, 3RS)-1-(Cyclohexylmethyl)-4-ethyl-2,3-dihydroxyhexyl]-α-[(R)-α-(3,3-dimethyl-2-oxobutyl)hydrocinnamamido]imidazole-4-propionamide;

(S)-N-[(1S, 2R, 3S)-3-cyclohexyl-1-(cyclohexylmethyl)-2,3-dihydroxypropyl]-α-[(R)-α-(3,3-dimethyl-2-oxobutyl)hydrocinnamamido]imidazole-4-propionamide;

(S)-N-[(1S,2R,3S)-1-(cyclohexylmethyl)-2,3-dihydroxy-4-methylpentyl]-α-[(R)-α-(3,3-dimethyl-2-oxobutyl)hydrocinnamamido]imidazole-4-propionamide;

(S)-α-[(S)-α-[(t-butylsulphonyl)methyl]hydrocinnamamido]-N-[(1S,2R,3S)-1-(cyclohexylmethyl)-2,3-dihydroxy-3-phenylpropyl]imidazole-4-propionamide;

(S)-α-[(S)-α-[(t-butylsulphonyl)methyl]hydrocinnamamido]-N-[(1S,2R,3R)-1-(cyclohexylmethyl)-2,3-dihydroxy-3-phenylpropyl]imidazole-4-propionamide;

(S)-α-[(S)-α-[(t-butylsulphonyl)methyl]hydrocinnamamido]-N-[(1S,2R,3RS)-1-(cyclohexylmethyl)-2,3-dihydroxy-4,4-dimethylpentyl]imidazole-4-propionamide;

(S)-α-[(S)-α-[(t-butylsulphonyl)methyl]hydrocinnamamido]-N-[(1S,2R,3S)-1-(cyclohexylmethyl)-2,3-dihydroxy-4-methylpentyl]imidazole-4-propionamide;

(S)-α-[(S)-α-[(t-butylsulphonyl)methyl]hydrocinnamamido]-N-[(1S,2R,3S)-3-cyclohexyl-1-(cyclohexylmethyl)-2,3-dihydroxypropyl]imidazole-4-propionamide.

Further especially preferred compounds of formula I are:

(S)-α-[(S)-α-[(t-Butylsulphonyl)methyl]hydrocinnamamido]-N-[(1S, 2R, 3RS)-1-(cyclohexylmethyl)-2,3-dihydroxy-3-(2-furyl)propyl]imidazole-4-propionamide:

(S)-N-[(1S,2R,3R or S)-1-(cyclohexylmethyl)-2,3-dihydroxy-3-[(R or S)-tetrahydro-2-furyl]propyl]-α-[(R)-α-(3,3-dimethyl-2-oxobutyl)hydrocinnamamido]-imidazole-4-propionamide;

(S) -α-[(S) -α-[(t-butylsulphonyl)methyl]hydrocinnamamido]-N-[(1S,2R,3R or S,Z)-1-(cyclohexylmethyl)-2,3-dihydroxy-4-methyl-4-hexenyl]imidazole-4-propionamide.

Still further especially preferred compounds of formula I are:

(S)-N-[(1S,2R,3S)-1-(Cyclohexylmethyl)-3-cyclopropyl-2,3-dihydroxypropyl]-α-[(S)-α-[(morpholinocarbonyl)-methyl]hydrocinnamamido]imidazole-4-propionamide;

(S) -α-[(S)-α-[(t-butylsulphonyl)methyl]-1-naphthalene-propionamido]-N-[(1S, 2R, 3S)-1-(cyclohexylmethyl)-3-cyclopropyl-2,3-dihydroxypropyl]imidazole-4-propionamide;

(S) -α-[(S)-2-[(t-butylsulphonyl)methyl]-4-phenylbutyramido]-N-[(1S, 2R, 3S)-1-( cyclohexylmethyl )-3-cyclopropyl-2,3-dihydroxypropyl]imidazole-4-propionamide;

(S) -α-[(R) -α-[(t-butylsulphonyl)methyl]hydrocinnamamido]-N-[(1S, 2R, 3S) -1-( cyclohexylmethyl )-3-cyclopropyl-2,3-dihydroxypropyl]imidazole-4-propionamide;

(S)-N-[(S)-1-[(2R or S,4R,5S)-2-t-butyl-5-isopropyl-1,3-dioxolan-4-yl ]-2-cyclohexylethyl ]-α-[(S)-α-[(t-butylsulphonyl)methyl]hydrocinnamamido]imidazole-4-propionamide;

(1R, 2S)-1-[(S)-1-[[N-[(S)-α-[(t-butylsulphonyl)methyl]-cinnamoyl]-L-histidyl]amino]-2-cyclohexylethyl]-2-cyclopropylethylene bis(methoxyacetate).

Quite especially preferred compounds of formula I are:

(S)-N-[(1S, 2R, 3S)-1-(Cyclohexylmethyl)-3-cyclopropyl-2,3-dihydroxypropyl]-α-[(R)-α-(3,3-dimethyl-2-oxo-butyl)hydrocinnamamido]imidazole-4-propionamide;

(S)-α-[(S)-α-[(t-butylsulphonyl)methyl]hydrocinnamamido]—N—[(1S,2R,3S)-1-(cyclohexylmethyl)-3-cyclopropyl-2,3-dihydroxypropyl]imidazole-4-propionamide;

(S)-α-[(S)-α-[(t-butylsulphonyl)methyl]hydrocinnamamido]—N—[(1S,2R,3S)-3-cyclobutyl-1-(cyclohexylmethyl)-2,3-dihydroxypropyl]imidazole-4-propionamide;

(S)—N—[(S)-1-[(4R,5S)-2-t-butyl-5-cyclopropyl-1,3-dioxolan-4-yl]-2-cyclohexylethyl]-α-[(S)-α-[(t-butylsulphonyl)methyl]hydrocinnamamido]imidazole-4-propionamide;

(1S,2R)-[(S)-1-[(S)-α-[(S)-α-[(t-butylsulphonyl)methyl]hydrocinnamamido]imidazole-4-propionamido]-2-cyclohexylethyl]-1-isopropylethylene bis(methoxyacetate);

(S)-α-[(S)-α-[(t-butylsulphonyl)methyl]hydrocinnamamido]—N—[(1S,2R,3S)-1-(cyclohexylmethyl)-3-cyclopentyl-2,3-dihydroxypropyl]imidazole-4-propionamide;

(S)-α-[(S)-α-[(t-butylsulphonyl)methyl]hydrocinnamamido]—N—[(1S,2R,3S)-1-(cyclohexylmethyl)-3-cyclopropyl-2,3-dihydroxypropyl]-4-thiazolepropionamide;

(S)-α-[(S)-α-[(t-butylsulphonyl)methyl]hydrocinnamamido]—N—[(1S,2S or R,3S or R,4SR)-1-(cyclohexylmethyl)-2,3,5-trihydroxypentyl]imidazole-4-propionamide.

The compounds of formula I in the form of optically pure diastereomers, mixtures of diastereomers, diastereomeric racemates or mixtures of diastereomeric racemates as well as pharmaceutically usable salts thereof can be manufactured by a) reacting a compound of the formula

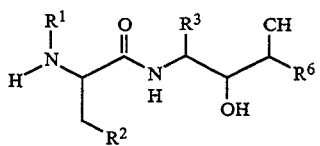

wherein $R^1$, $R^2$, $R^3$ and $R^6$ have the significance given above, with an acylating agent yielding the group

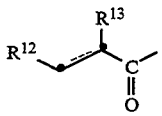 (c)

or

—Y—Z  (d), wherein $R^{12}$, $R^{13}$, Y, Z and the dotted line have the significance given above, or b) reacting a compound of the formula

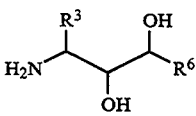 III wherein $R^3$ and $R^6$ have the significance given above, with a compound of the formula

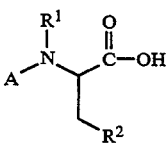 IV wherein $R^1$, $R^2$ and A have the significance given above, or an activated derivative thereof, or c) reacting a compound of formual I in which $R^4$ and $R^5$ each signify hydrogen and the remaining symbols have the significance given above with an alkanoylating agent, which is optionally mono- or multiply-substituted by amino, monoalkylamino, dialkylamino, alkanoylamino, alkanoyloxyamino, carboxy, alkoxy or hydroxy, or with an agent forming an O-protecting group, and d) if desired, separating a mixture of diastereomeric racemates into the diastereomeric racemates or optically pure diastereomers, and/or e) if desired, separating a mixture of diastereomers into the optically pure diastereomers, and/or f) if desired, converting a compound obtained into a pharmaceutically usable salt.

The acylation of a compound of formula II is effected according to methods known per se. Especially suitable acylating agents are activated acid derivatives such as esters, mixed esters, acid halides and acid anhydrides or mixed anhydrides. The reaction is carried out in an organic solvent or solvent mixture which is inert under the reaction conditions at a temperature between about 0° C. and room temperature. As solvents there come into consideration especially aromatic hydrocarbons such as benzene, toluene or xylene, chlorinated hydrocarbons such as methylene chloride or chloroform, ethers such as diethyl ether, tetrahydrofuran or dioxan, and the like. Where the acylating agent is a dipeptide, the reaction is effected under reaction conditions which are usual in peptide chemistry, i.e. preferably in the presence of a condensing agent such as HBTU (O-benzotriazolyl-N,N,N',N'-tetramethyluronium hexafluorophosphate), BOP (benzotriazol-1-yloxy bis-(dimethylamino)phosphonium hexafluorophosphate), HOBT (N-hydroxybenzotriazole), DBU (1,8-diazabicyclo[5.4.0]undec-7-ene), DCC (dicyclohexylcarbodiimide), EDC (N-ethyl-N'(3-dimethylaminopropyl)carbodiimide hydrochloride), Hünig base (ethyldiisopropylamine) and the like. The reaction is conveniently carried out in an organic solvent or solvent mixture which is inert under the reaction conditions at a temperature between about 0° and 50° C., preferably at about room temperature. As solvents there come into consideration especially dimethylformamide, methylene chloride, acetonitrile, tetrahydrofuran and the like.

The reaction of a compound of formula III with a compound of formula IV is also effected according to methods which are known per se in peptide chemistry, i.e. under the same conditions as have been given above for the reaction of a compound of formula II with a dipeptide. Examples of suitable activated derivatives of a compound of formula IV are acid halides, acid anhydrides, acid azides, mixed anhydrides, esters, mixed esters, and the like.

The reaction of a compound of formula I in which $R^4$ and $R^5$ each signify hydrogen with an alkanoylating agent is also effected according to methods known per se. Suitable alkanoylating agents are alkanoic acid anhydrides and halides, preferably chlorides. The reaction is effected in an organic solvent or solvent mixture which is inert under the reaction conditions at a temperature between about room temperature and the reflux temperature of the reaction mixture, preferably at about room temperature. The reaction can be carried out in the presence or absence of an acid-binding agent such as sodium or potassium carbonate, pyridine, triethylamine and the like. The reaction of a compound of formula I in which $R^4$ and $R^5$ each signify hydrogen with an agent forming an O-protecting group is also effected in a manner known per se. Thus, for example, the tetrahydropyranyl ether can be manufactured by reaction with dihydropyran in the presence of an acid catalyst such as p-toluenesulphonic acid and the like and the acetone ketal can be manufactured by reaction with 2,2-dimethoxypropane in the presence of an acid catalyst such as p-toluenesulphonic acid.

The starting materials of formula II are novel and are also an object of the present invention. These compounds can be prepared by reacting a compound of formula III with optionally N-methylated histidine, leucine, norleucine, norvaline, thiazolylalanine, thienylalanine or t-butoxyserine. This reaction is also effected according to methods which are known in peptide chemistry, i.e. under the reaction conditions described above for the reaction of a compound of formula II with a dipeptide.

The starting materials of formula III are also novel and are an object of the present invention. They can be prepared, for example, by cleaving off the amino protecting group and, if desired, simultaneously also the O-protecting group in a compound of the formula

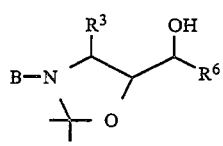

V or

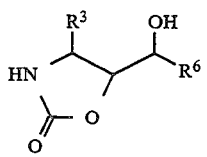

VI wherein B signifies an amino protecting group, preferably t-butoxycarbonyl or benzyloxycarbonyl, and $R^3$ and $R^6$ have the significance given above, or by treating a compound of the formula

VII wherein $R^3$ and $R^6$ have the significance given above, with a base.

The cleavage of the N-protecting group and optionally of the O-protecting group is also effected according to methods known per se, for example in an organic solvent or solvent mixture which is inert under the reaction conditions at a temperature between about 0° C. and room temperature with an acid such as hydrochloric acid, trifluoroacetic acid, and the like. Suitable solvents are ethers such as tetrahydrofuran or dioxan, alcohols such as methanol or chlorinated hydrocarbons such as methylene chloride, and the like. Under these reaction conditions the oxazolidine ring in a compound of formula VI is—as already mentioned—simultaneously cleaved.

The reaction of a compound of formula VII with a base is also effected according to methods known per se in a solvent or solvent mixture which is inert under the reaction conditions at a temperature between about room temperature and the reflux temperature. Suitable solvents are, for example, methanol, ethanol, dioxan, tetrahydrofuran, water or mixtures thereof. As bases there conveniently come into consideration sodium, potassium or barium hydroxide and the like.

The starting materials of formula IV are known or can be obtained in analogy to the preparation of the known compounds.

The compounds of formulae V and VI are also novel and are objects of the present invention. They can be prepared, for example, by reducing the corresponding keto compounds of the formula

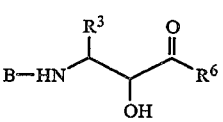

VIII or

-continued

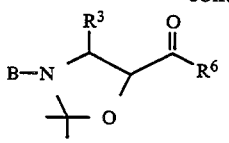

wherein B, $R^3$ and $R^6$ have the significance given above.

The reduction of a keto compound of formula VIII or IX is also effected according to methods known per se, for example with a complex metal hydride such as sodium borohydride and the like, in an organic solvent or solvent mixture which is inert under the reaction conditions at a temperature between about 0° C. and about room temperature.

The compounds of formula VII are also novel and are an object of the present invention. They can be prepared, for example, by reacting the corresponding formyl compounds of the formula

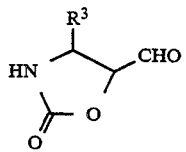

wherein $R^3$ has the significance given above, with a metal-organic compound yielding the residue $R^6$.

The reaction with a metal-organic compound is also effected according to methods known per se, for example in a solvent which is inert under the reaction conditions, such as an ether, at a temperature between about $-100°$ C. and 50° C. depending on the nature of the metal-organic compound which is used. If a lithium compound is used, the reaction is preferably effected at about $-50°$ C. to about $-80°$ C., while the reaction is preferably carried out at about room temperature when a Grignard compound is used.

The compounds of formulae VIII, IX and X are also novel and are objects of the present invention. The compounds of formula VIII can be prepared, for example, by reacting an ester or a cyanohydrin of the formula

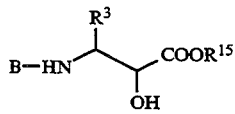

or

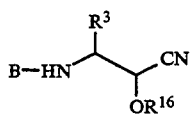

wherein B and $R^3$ have the significance given above, $R^{15}$ signifies alkyl and $R^{16}$ preferably signifies trimethylsilyl, with a compound of the formula

wherein $R^6$ has the significance given above and W signifies chlorine, bromine or iodine, preferably bromine, in a Grignard reaction. This reaction is also effected according to methods known per se, for example in a solvent which is inert under the reaction conditions, such as an ether, at a temperature between about 0° C. and 50° C., preferably at room temperature. Where a compound of formula XII is used, the imine which occurs as an intermediate must be hydrolyzed with a weak aqueous acid such as phosphoric acid, whereby simultaneously the trimethylsilyl group is cleaved off.

The compounds of formula IX can be prepared by, for example, reacting an ester of the formula

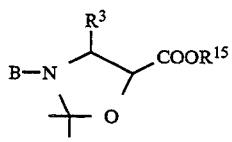

wherein B, $R^3$ and $R^{15}$ have the significance given above, with a lithium compound of the formula

wherein $R^6$ has the significance give above. This reaction is also effected according to methods known per se, for example in a solvent which is inert under the reaction conditions, such as an ether, at a temperature between about $-100°$ C. and 0° C., preferably at about $-70°$ C.

The compounds of formula X are also novel and are an object of the present invention. They can be prepared, for example, by subjecting a compound of the formula

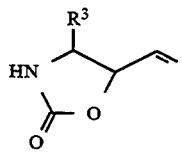

wherein $R^3$ has the significance given above, to a reductive ozonolysis. The reaction with ozone is also effected according to methods known per se, for example in methanol or methylene chloride as the solvent at a temperature between about $-100°$ C. and $-20°$ C. The subsequent reduction of the ozonide is also effected according to methods known per se, for example by adding dimethyl sulphide at a temperature between about $-50°$ C. and room temperature.

The compounds of formula XI, XII, XIII, XIV, XV and XVI are known or can be obtained in analogy to the preparation of the known compounds.

A further process for the preparation of the compounds of formula V comprises oxidizing a compound of the formula

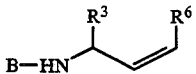

wherein B, $R^3$ and $R^6$ have the significance given above. The oxidation of a compound of formula XVII is also effected according to methods known per se in an organic solvent or solvent mixture which is inert under the reaction conditions at a temperature between about room temperature and the boiling point of the solvent or solvent mixture, preferably at about room temperature. Osmium tetroxide is the especially suitable oxidizing agent. As solvents there come into consideration especially pyridine and the like.

The compounds of formula XVII are also novel and are an object of the present invention. They can be prepared according to methods known per se, for example by reacting an aldehyde of the formula

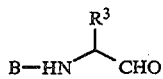
XVIII wherein B and $R^3$ have the significance given above, with a corresponding Wittig reagent. The reaction is also carried out according to known methods, for example in a solvent which is inert under the reaction conditions, such as an ether, at a temperature between about $-50°$ C. and room temperature.

The compounds of formula XVIII as well as the corresponding Wittig reagents are known or can be obtained in analogy to the preparation of the known compounds.

In accordance with an alternative process a compound of formula VI can also be prepared by reacting a compound of the formula

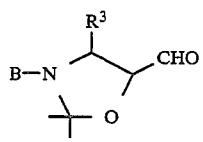
XIX wherein B and $R^3$ have the significance given above, in a Grignard reaction with a compound of formula XIII, i.e. under the same conditions as given above for the reaction of a compound of formula XI with a compound of formula XIII.

The compounds of formula XIX are known or can be prepared in analogy to the known compounds.

The various processes for the preparation of the compounds of formulae III, V, VI and VII starting from a compound of formula XVIII are compiled in Scheme I hereinafter.

Scheme I
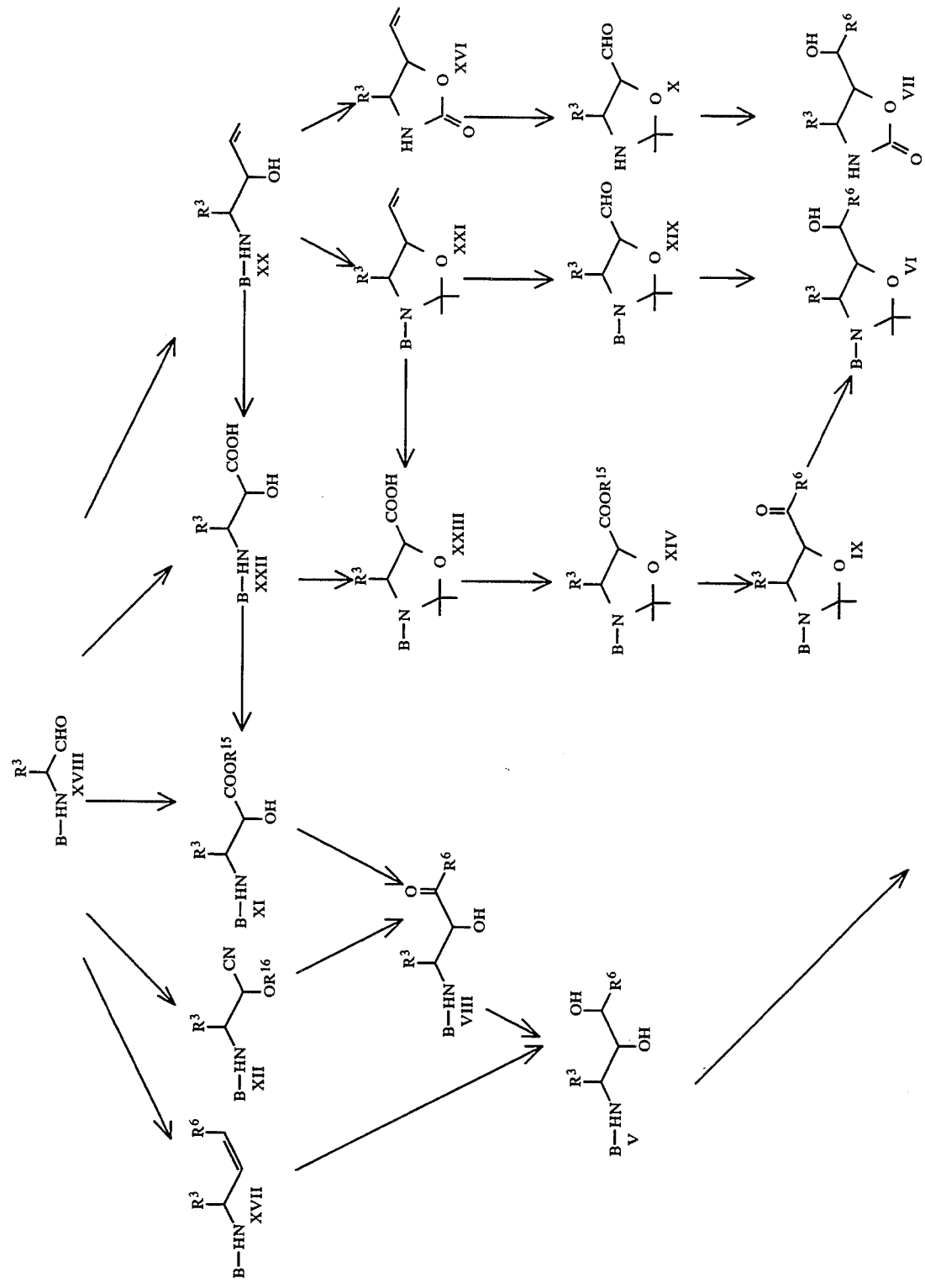

Scheme I -continued
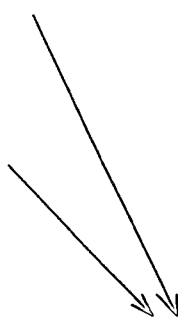
III

The compounds of formula I and their pharmaceutically usable salts have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angiotensin II increases the blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II itself or to the heptapeptide angiotensin III which is formed therefrom as a cleavage product. Inhibitors of the enzymatic activity of renin bring about a decrease in the formation of angiotensin I and as a consequence thereof the formation of a smaller amount of angiotensin II. The reduced concentration of this active peptide hormone is the actual reason for the blood pressure-lowering activity of renin inhibitors.

The activity of renin inhibitors can be demonstrated experimentally by means of the in vitro test described hereinafter:

In vitro test with pure human renin

The test is carried out in Eppendorf test tubes. The incubation mixture consists of (1) 100μl of human renin in buffer A (0.1M sodium phosphate solution, pH 7.4, containing 0.1% bovine serum albumin, 0.1% sodium azide and 1 mM ethylenediaminetetraacetic acid), sufficient for a renin activity of 2—3 ng of angiotensin I/ml/hr.; (2) 145 μl of buffer A; (3) 30 μl of 10 μM human tetradecapeptide renin substrate (hTD) in 10 mM hydrochloric acid; (4) 15 μl of dimethyl sulphoxide with or without inhibitor and (5) 10 μl of a 0.03 molar solution of hydroxyquinoline sulphate in water.

The samples are incubated for 3 hours at 37° C. or 4° C. in triplicate. 2 ×100 μl samples per experimental test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I is determined by the difference between the experiment at 37° C. and that at 4° C.

The following controls are carried out:

(a) Incubation of hTD samples without renin and without inhibitor at 37° C. and 4° C. The difference between these two values gives the base value of angiotensin I production.

(b) Incubation of hTD samples with renin, but without inhibitor at 37° C. and 4° C. The difference between these values gives the maximal-value of angiotensin I production.

In each sample the base value of the angiotensin I production is subtracted from the angiotensin I production which is determined. The difference between the maximal value and the base value gives the value of the maximal substrate hydrolysis (=100%) by renin.

The results are given as $IC_{50}$ values which denote that concentration of the inhibitor at which the enzymatic activity is inhibited by 50%. The $IC_{50}$ values are determined from a linear regression curve from a logit-log plot.

The results obtained in this test are compiled in the following Table:

TABLE

| Compound | $IC_{50}$ values in μMol/lt. |
|---|---|
| A | 0.024 |
| B | 0.001 |
| C | 0.003 |
| D | 0.007 |
| E | 0.17 |
| F | 0.038 |
| G | 0.002 |
| H | 0.002 |

A = (S)-N-[(1S,2R,3RS)-1-(Cyclohexylmethyl)-4-ethyl-2,3-dihydroxyhexyl]-α-[(R)-α-(3,3-dimethyl-2-oxobutyl)hydrocinnamamido]imidazole-4-propionamide;

B = (S)-N-[(1S,2R,3S)-3-cyclohexyl-1-(cyclohexylmethyl)-2,3-dihydroxypropyl]-α-[(R)-α-(3,3-dimethyl-2-oxobutyl)-hydrocinnamamido]imidazole-4-propionamide;

C = (S)-N-[(1S,2R,3S)-1-(cyclohexylmethyl)-2,3-dihydroxy-4-methylpentyl]-α-[(R)-α-(3,3-dimethyl-2-oxobutyl)hydrocinnamamido]imidazole-4-propionamide;

D = (S)-α-[(S)-α-[(t-butylsulphonyl)methyl]hydrocinnamamido]-N-[(1S,2R,3S)-1-(cyclohexylmethyl)-2,3-dihydroxy-3-phenylpropyl]imidazole-4-propionamide;

E = (S)-α-[(S)-α-[(t-butylsulphonyl)methyl]hydrocinnamamido]-N-[(1S,2R,3R)-1-(cyclohexylmethyl)-2,3-dihydroxy-3-phenylpropyl]imidazole-4-propionamide;

F = (S)-α-[(S)-α-[(t-butylsulphonyl)methyl]hydrocinnamamido]-N-[(1S,2R,3RS)-1-(cyclohexylmethyl)-2,3-dihydroxy-4,4-dimethylpentyl]imidazole-4-propionamide;

G = (S)-α-[(S)-α-[(t-butylsulphonyl)methyl]hydrocinnamamido]-N-[(1S,2R,3S)-1-(cyclohexylmethyl)-2,3-dihydroxy-4-methylpentyl]imidazole-4-propionamide;

H = (S)-α-[(S)-α-[(t-butylsulphonyl)methyl]hydrocinnamamido]-N-[(1S,2R,3S)-3-cyclohexyl-1-(cyclohexylmethyl)-2,3-dihydroxypropyl]imidazole-4-propionamide.

The compounds of formula I as well as their pharmaceutically usable salts can be used as medicaments, e.g. in the form of pharmaceutical preparations. The pharmaceutical preparations can be administered enterally such as orally, e.g. in the form of tablets, coated tablets, dragees, hard and soft gelatine capsules, solutions, emulsions or suspensions, nasally, e.g. in the form of nasal sprays, or rectally, e.g. in the form of suppositories. However, the administration can also be effected parenterally such as intramuscularty or intravenously, e.g. in the form of injection solutions.

For the manufacture of tablets, coated tablets, dragees and hard gelatine capsules the compounds of formula I as well as their pharmaceutically usable salts can be processed with pharmaceutically inert, inorganic or organic excipients. Lactose, maize starch or derivatives thereof, talc, stearic acid or its salts etc can be used e.g. as such excipients for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preserving agents, solubilizers, viscosity-increasing substances, stabilizing agents, wetting agents, emulsifying agentd, sweetening agents, colouring agents, flavouring agentd, salts for varying the osmotic pressure, buffers, coating agents or antioxidants. They can also contain stillother therapeutically valuable substances.

In accordance with the invention the compounds of formula I as well as their pharmaceutically usable salts can be used in the control or prevention of high blood pressure and cardiac insufficiency. The dosage can vary within wide limits and will, of course, be fitted to the individual requirements in each particular case. In general, in the case of oral administration there should suffice a daily dosage of about 3 mg to about 3 g, preferably about 10 mg to about 1 g, e.g. approximately 300 mg per person, divided in preferably 1–3 unit doses, which can e.g. be of the same amount, whereby, however, the upper limit just given can also be exceeded when this is found to be idicated. Usually, children receive half of the dosage of adults.

The following Examples are intended to illustrate the present invention, but are not intended to be limiting in any manner. All temperatures are given in degrees Celsius. The following abbreviations are used:
H—His—OH = L-histidine
Boc = t-butoxycarbonyl
Fmoc = 9-fluorenylmethoxycarbonyl

EXAMPLE 1

A mixture of 880 mg (2.3 mmol) of (S)-α-amino—N—[(1S, 2R, 3RS)-1(cyclohexylmethyl)-4-ethyl-2,3-dihydroxyhexyl]imidazole-4-propionamide, 608 mg (2.45 mmol) of (R)-α-(pivaloylmethyl)hydrocinnamic acid (see EPA 0 184 550), 0.35 ml (2.76 mmol) of 4-ethylmorpholine, 662 mg (4.9 mmol) of HBT amd 529 mg (2.76 mmol) of EDC in 20 ml of dimethylformamide is stirred at room temperature overnight. Thereafter, the reaction mixture is evaporated to dryness in a high vacuum, the residue is poured into a mixture of ice and 2N sodium bicarbonate solution and extracted three times with ethyl acetate. The extracts are washed in succession with saturated ammonium chloride solution, 2N sodium bicarbonate solution and saturated sodium chloride solution and combined. After drying the organic solution over magnesium sulphate the solvent is evaporated under reduced pressure and the residue (1.01 g), for purification, is chromatographed on 70 g of silica gel using a 20:1:0.1 mixture of methylene chloride, methanol and ammonia as the eluting agent. Crystallization of the thus-obtained crude product from methylene chloride/methanol/ether yields 900 mg of (S)—N—[(1S,2R,3RS)-1-(cyclohexylmethyl)-4-ethyl-2,3-dihydroxyhexyl]-α-[(R)-α-(3,3-dimethyl-2-oxobutyl)-hydrocinnamamido]imidazole-4-propionamide, melting point 160°, MS: 624 (M)+.

The (S)-α-amino—N—[(1S,2R,3RS)-1-(cyclohexylmethyl)-4-ethyl-2,3-dihydroxyhexyl]imidazole-4-propionamide used as the starting material was prepared as follows:

A mixture of 87.9 g (300 mmol) of 2-t-butoxycarbonylamino-3(S)-cyclohexylpropylaldehyde, prepared in turn according to the method described by J. Boger et al. in J. Med. Chem., 28, 1779 (1985), 1.2 g of a 1:1 mixture of potassium cyanide and 18-crown-6 (that is, 1,4,7,10,13,16-hexaoxacyclooctadecane) and 65 ml (520 mmol) of trimethylsilyl cyanide is stirred at room temperature for 1 hour in an argon atmosphere. The reaction mixture is then evaporated to dryness and the residue is treated twice in succession firstly with toluene and thereafter again evaporated to dryness. The residue is dissolved in a mixture of 200 ml of glacial acetic acid and 200 ml of conc. hydrochloric acid and the reaction mixture is heated to reflux overnight. Thereafter, the reaction mixture is evaporated under reduced pressure and the residue is partitioned between 800 ml of water and 800 ml of ether. The organic phase is washed twice with 400 ml of water and the aqueous washing is combined with the aqueous phase. The water is then evaporated and the residue is treated twice in succession firstly with toluene and thereafter again evaporated to dryness. 23.94 ml (330 mmol) of thionyl chloride are added dropwise to the residue (83.7 g), which has been dissolved in 1 l of methanol, in an argon atmosphere while stirring and at a temperature between −10° and −20° within 30 minutes. After completion of the addition the reaction mixture is stirred at room temperature overnight and thereafter evaporated to dryness under reduced pressure. The residue is treated twice in succession firstly with toluene and thereafter again evaporated to dryness. A mixture of the thus-obtained residue in 500 ml of dimethylformamide, 188 ml (1.35 mol) of triethylamine and 78 g (0.36 mol) of di-t-butyl dicarbonate is stirred at room temperature overnight and thereafter evaporated in a high vacuum. The residue is extracted three times with 1.8 l of ethyl acetate each time. The three organic extracts are washed in succession with in each case 900 ml of ice-cold 1N sulphuric acid, 900 ml of 2N sodium bicarbonate solution and 900 ml of water, combined, dried over magnesium sulphate and evaporated. Chromatography of the thus-obtained crude product on 1.5 kg of silica gel with a 92:8 mixture of toluene and ethyl acetate as the eluting agent yields 13.14 g of t-butyl [(1S,2R)-1-(cyclohexylmethyl)-2-hydroxy-3-(methoxycarbonyl)ethyl]carbamate as an oil, MS: 315 (M)+, as well as 10.6 g of the less polar epimer t-butyl [(1S,2S)-1-(cyclohexylmethyl)-2-hydroxy-3-(methoxycarbonyl)ethyl] carbamate also as an oil, MS: 315 (M)+.

A solution of 2.72 g (7.57 mmol) of t-butyl [(1S,2R)-1-(cyclohexylmethyl)-2hydroxy-3-(methoxycarbonyl)ethyl] carbamate in 70 ml of tetrahydrofuran is added dropwise at about 30° to a solution of the Grignard compound prepared from 44.18 ml (345 mmol) of 3-bromopentane (97%) and 8.39 g (345 gram atom) of magnesium shavings in 280 ml of tetrahydrofuran and the reaction mixture is subsequently stirred at room temperature under argon for 70 hours. Thereafter, the reaction mixture is poured into 100 ml of an ice-cold saturated ammonium chloride solution, the organic phase is separated and the aqueous phase is extracted a further two times with 300 ml of ether each time. The two ether extracts are washed with in each case 100 ml of saturated ammonium chloride solution, combined and dried over magnesium sulphate. The solvent is then evaporated under reduced pressure and the residue is chromatographed on 250 g of silica gel with a 4:1 mixture of hexane and ether as the eluting agent, whereby there are obtained 180 mg of t-butyl [(1S,2R)-1-(cyclohexylmethyl)-4-ethyl-2-hydroxy-3-oxohexyl] carbamate as an oil, MS: 355 (M)+.

320 mg (0.9 mmol) of t-butyl [(1S,2R)-1-(cyclohexylmethyl)-4-ethyl-2-hydroxy-3-oxohexyl] carbamate in 10 ml of ethanol are stirred at room temperature for 3 hours with 34 mg (0.9 mmol) of sodium borohydride. Thereafter, 0.5 ml of acetic acid is added, the reaction mixture is evaporated and the residue is extracted three times with 150 ml of ethyl acetate each time. The three organic extracts are then washed with in each case 70 ml of 2N sodium bicarbonate solution and 70 ml of saturated sodium chloride solution, combined, dried over magnesium sulphate, filtered and evaporated. For purification, the residue is chromatographed on 30 g of silica gel using a 7:3 mixture of hexane and ether as the eluting agent, whereby there are obtained 260 mg of t-butyl [(1S,2R,3RS)-1-(cyclohexylmethyl)-4-ethyl-2,3-dihydroxyhexyl] carbamate as an oil, MS: 357 (M)+.

540 mg (1.51 mmol) of t-butyl [(1S,2R,3RS)-1-(cyclohexylmethyl)-4-ethyl-2,3-dihydroxyhexyl] carbamate in 20 ml of 1.58N hydrochloric acid in dioxan are left to stand at room temperature overnight. The reaction mixture is thereafter evaporated and the residue is treated twice in succession firstly with toluene and then again evaporated to drynedd. A misture of the thus-obtained crude product with 995 mg (1.66 mmol) of (Fmoc)₂His—OH, 0.42 ml (3.22 mmol) of 4-ethylmorpholine, 449 mg (3.22 mmol) of HBT and 347 mg (1.81 mmol) of EDC in 20 ml of dimethylformamide is left to stand at room temperature overnight. Thereafter, the reaction mixture is evaporated in a high vacuum, the residue is poured into a mixture of ice and 90 ml of 2N sodium bicarbonate solution and extracted three times with 150 ml of ethyl acetate each time. The three ethyl acetate extracts are washed in succession with 70 ml of saturated ammonium chloride solution, 70 ml of 2N sodium bicarbonate solution and 70 ml of saturated sodium chloride solution, combined, dried over magnesium sulphate, filtered and evaporated. The obtained crude product (2.2 g) is stirred at room temperature for 3 hours in 60 ml of methylene chloride and 2 ml of piperidine. The reaction mixture is then evaporated and the residue is triturated from 50 ml of hexane and filtered off. The filtrate is chromatographed on 70 g of silica gel with a 8:1:0.1 mixture of methylene chloride, methanol and ammonia as the eluting agent, whereby there are obtained 880 mg of (S)-α-amino—N—[(1S,2R,3RS)-1-(cyclohexylmethyl)-4-ethyl-2,3-dihydroxyhexyl]imidazole-4-propionamdie as a foam, MS: 394 (M)+.

EXAMPLE 2

The following compounds were manufactured in an analogous manner to that described in Example 1:

From (S)-α-amino—N—[(1S,2R,3S)-3-cyclohexyl-1-(cyclohexylmethyl)-2,3-dihydroxypropyl]imidazole-4-propionamide and (R)-α-(pivaloylmethyl)hydrocinnamic acid the (S)—N—[(1S,2R,3S)-3-cyclohexyl-1-(cyclohexylmethyl)- 2,3-dihydroxypropyl]-α-[(R)-α-(3,3-dimethyl-2-oxobutyl)hydrocinnamamido]imidazole-4-propionamide as a white solid, melting point >175° (dec.; from methylene chloride/methanol/hexane), MS: 636 (M)+;

from (S)-α-amino—N—[(1S,2R,3S)-3-cyclohexyl-1-(cyclohexylmethyl)-2,3-dihydroxypropyl]imidazole-4-propionamide and (S)-α-[(t-butylsulphonyl)methyl]hydrocinnamic acid (see EPA 0,236 734) the (S)-α-[(S)-α-[(t-butylsulphonyl)methyl]hydrocinnamamido]—N—[(1S,2R,3S)-3-cyclohexyl-1-(cyclohexylmethyl)-2,3-dihydroxypropyl]imidazole-4-propionamide, MS: 673 (M+1)+;

from (S)-α-amino—N—[(1S,2R,3S)-1-(cyclohexylmethyl)-2,3-dihydroxy-4-methylpentyl]imidazole-4-propionamide and (R)-α-(pivaloylmethyl)hydrocinnamic acid the (S)—N—[(1S,2R,3S)-1-(cyclohexylmethyl)-2,3-dihydroxy-4-methylpentyl]-α-[(R)-α-(3,3-dimethyl-2-oxobutyl)hydrocinnamamido]imidazole-4-propionamide as a solid of melting point 153° (from methylene chloride/methanol/hexane);

from (S)-α-amino—N—[(1S,2R,3S)-1-(cyclohexylmethyl)-2,3-dihydroxy-4-methylpentyl]imidazole-4-propionamide and (S)-α-[(t-butylsulphonyl)methyl]hydrocinnamic acid the (S)-α-[(S)-α-[(t-butylsulphonyl)methyl]-hydrocinnamamido]—N—[(1S,2R,3S)-1-(cyclohexylmethyl)-2,3-dihydroxy-4-methylpentyl]imidazole-4-propionamide as a white solid, melting point 114° (dec.; from methylene chloride/ether), MS: 597 (M+1)+.

The propionamides used as the starting materials were prepared as follows:

(S)-α-Amino—N—[(1S,2R,3S)-3-cyclohexyl-1-(cyclohexylmethyl)-2,3-dihydroxypropyl]imidazole-4-propionamide In an analogous manner to that described in Example 1, t-butyl [(1S,2R)-1-(cyclohexylmethyl)-2-hydroxy-3-(methoxycarbonyl)ethyl] carbamate is reacted in a Grignard reaction with cyclohexylmagnesium bromide to give t-butyl [(1S,2R)-3-cyclohexyl-1-(cyclohexylmethyl)-2-hydroxy-3-oxopropyl] carbamate which, after reduction with sodium borohydride and chromatographic separation of the isomers obtained carried out in an analogous manner to Example 1, yields t-butyl [(1S,2R,3S)-3-cyclohexyl-1-(cyclohexylmethyl)-2,3-dihydroxypropyl] carbamate. Then, again in an analogous manner to that described in Example 1, the Boc protecting group is cleaved off with hydrochloric acid in dioxan, the crude product obtained is reacted with (Fmoc)₂His—OH and the two protecting groups are cleaved off with piperidine.

(S)-α-Amino—N—[(1S,2R,3S)-1-cyclohexylmethyl)-2,3-dihyroxy-4-methylpentyl]imidazole-4-propionamide This compound was obtained, also in an analogous manner to that described in Example 1, by reacting t-butyl [(1S,2R)-1-(cyclohexylmethyl)-2-hydroxy-3-(methoxycarbonyl)-ethyl] carbamate with isopropylmagnesium bromide, reducing the t-butyl [(1S,2R)-1-(cyclohexylmethyl)-2-hydroxy-4-methyl-3-oxopentyl] carbamate obtained with sodium borohydride, separating the isomers obtained by chromatography, cleaving off the Boc protecting group from t-butyl [(1S,2R,3S)-1-(cyclohexylmethyl)-2,3-dihydroxy-4-methylpentyl] carbamate with hydrochloric acid in dioxan, reacting with (Fmoc)₂His—OH and cleaving off the two protecting groups with piperidine.

EXAMPLE 3

The following compounds were manufactured in an analogous manner to that described in Example 1:

From (S)-α-amino—N—[(1S,2R,3S)-1-(cyclohexylmethyl)-2,3-dihydroxy-3-phenylpropyl]imidazole-4-propionamide and (S)-α-[(t-butylsulphonyl)methyl]hydrocinnamic acid the (S)-α-[(S)-α-[(t-butylsulphonyl)methyl]hydrocinnamamido]—N—[(1S,2R,3S)-1-(cyclohexylmethyl)-2,3-dihydroxy-3-phenylpropyl]imidazole-4-propionamide as a white solid of melting point 112° (from methylene chloride/diethyl ether/hexane) as well as from (S)-α-amino—N—[(1S,2R,3R)-1-(cyclohexylmethyl)-2,3-dihydroxy-3-phenylpropyl]imidazole-4-propionamide and (S)-α-[(t-butylsulphonyl)methyl]hydrocinnamic acid the epimeric (S)-α-[(t-butylsulphonyl)methyl]-hydrocinnamamido]—N—[(1S,2R,3R)-1-(cyclohexylmethyl-2,3-dihydroxy-3-phenylpropyl]imidazole-4-propionamide as a white solid of melting point 111° (dec.; from methylene chloride/diethyl ether);

from (S)-α-amino—N—[(1S,2R,3RS)-1-(cyclohexylmethyl)-2,3-dihydroxy-4,4-dimethylpentyl]imidazole-4- propionamide and (S)-α-[(t-butylsulphonyl)methyl]hydrocinnamic acid the (S)-α-[(S)-α-[(t-butylsulphonyl)methyl]hydrocinnamamido]—N—[(1S,2R,3RS)-1-(cyclohexylmethyl)-2,3-dihydroxy-4,4-dimethylpentyl]imidazole-4-propionamide as a white solid of melting point 210° (from methylene chloride/methanol/diethyl ether), MS: 646 (M)+.

The propionamides used as the starting materials were prepared as follows:

(S)-α-Amino—N—[(1S,2R,3S)-1-(cyclohexylmethyl)-2,3-dihydroxy-3-phenylpropyl]imidazole-4-propionamide and (S)-α-amino—N—[(1S,2R,3R)-1-(cyclohexylmethyl)-2,3-dihydroxy-3-phenylpropyl]imidazole-4-propionamide 7.5 g of t-butyl [(1S,2R)-1-(cyclohexylmethyl)-2-hydroxy-3-(methoxycarbonyl)ethyl] carbamate are stirred in 50 ml of dimethoxypropane at 50° overnight with 150 mg of p-toluenesulphonic acid. Thereafter, the reaction mixture is poured into ice-cold 2N sodium bicarbonate solution and extracted three times with 300 ml of ether each time. The three organic extracts are washed with water, combined, dried over magnesium sulphate and evaporated to dryness. The residual oil (8.43 g) is chromatographed on 250 g of silica gel with a 95:5 mixture of toluene and ethyl acetate as the eluting agent, containing 1% triethylamine, whereby there are obtained 7.06 g of 3-t-butyl 5-methyl (4S,5R)-4- (cyclohexylmethyl)-2,2-dimethyl-3,5-oxazolidinedicarboxylate as an oil, MS: 355 (M)+.

2.36 ml (2 mmol) of a 0.76N solution of phenyllithium in ether are sprayed at −75° into 355 mg (1 mmol) of 3-t-butyl 5-methyl (4S,5R)-4-(cyclohexylmethyl)-2, 2-dimethyl-3,5-oxazolidinedicarboxylate in 20 ml of ether and the reaction mixture is stirred at this temperature for 30 minutes, subsequently poured into 50 ml of saturated ammonium chloride solution and extracted three times with 150 ml of ether each time. The three ether extracts are washed in succession with in each case 70 ml of 2N sodium bicarbonate solution and 70 ml of saturated sodium chloride solution, combined, dried over magnesium sulphate, filtered and evaporated. The residual oil (540 mg) is chromatographed on 30 g of silica gel with a 98:2 mixture of toluene and ethyl acetate as the eluting agent, whereby there are obtained 300 mg of t-butyl (4S,5R)-5-benzoyl-4-(cyclohexylmethyl)-2,2-dimethyl-3-oxazolidinecarboxylate as a white solid, MS: 401 (M)+.

290 mg (0.72 mmol) of t-butyl (4S,5R)-5-benzoyl-4-(cyclohexylmethyl)-2,2-dimethyl-3-oxazolidinecarboxylate in 5 ml of methanol are stirred at room temperature for 1 hour with 27 mg (0.7 mmol) of sodium borohydride. Thereafter, the reaction mixture is treated with two drops of glacial acetic acid and evaporated to dryness. The residue is chromatographed on 30 g of silica gel with a 4:1 mixture of hexane and ether as the eluting agent, with a methylene chloride solution of the crude product being applied to the column, In this manner there are obtained 60 mg of t-butyl (4S, 5R)-4-(cyclohexylmethyl-5-[(S)-α-hydrozybenzyl]-2,2-dimethyl-3-oxazolidinecarboxylate as a white solid, MS: 403 (M)+, as well as 210 mg of the epimeric t-butyl (4S,5R)-4-(cyclohexylmethyl)-5-[(R)-α-hydroxybenzyl]-2,2-dimethyl-3-oxazolidinecarboxylate also as a white solid, MS: 403 (M)$^{30}$.

Thereafter, in each case the Boc protecting group is cleaved off from the two epimeric carboxylates with methanolic hydrochloric acid, the crude product obtained is coupled with (Fmoc)₂ His-OH and finally in each case the two protecting groups are removed with piperidine.

(S)-α-Amino—N—[(1S,2R,3RS)-1-(cyclohexylmethyl)-2, 3-dihydroxy- 4,4-dimethylpentyl]imidazole-4-propionamide In an analogous manner to that described above, by reacting 3-t-butyl 5-methyl (4S,5R)-4-(cyclohexylmethyl)-2,2-dimethyl-3,5-oxazolidinedicarboxylate with t-butyl-lithium there is prepared t-butyl (4S,5R)-4-(cycloxehyl-methyl)-2,2-dimethyl-5-pivaloyl-3-oxazolidinecarboxylate which is reduced with sodium borohydride to t-butyl (4S,5R)-4-(cyclohexylmethyl)-5-[(RS)-1-hydroxy-2,2-dimethyl-propyl]-2,2-dimethyl-3-oxazolidinecarboxylate. Cleavage of the Boc protecting group with methanolic hydrochloric acid, coupling with (Fmoc)₂His-OH and cleavage of the two protecting groups with piperidine yields (S)-α-amino—N—](1S,2R,3RS)-1-(cyclohexylmethyl)-2,3-dihydroxy-4,4-dimethylpentyl]imidazole-4-propionamide.

EXAMPLE 4

The following compounds were manufactured in an analogous manner to that described in Example 1:

From (S)-α-amino—N—[(1S,2R,3S)-1-(cyclohexylmethyl-3-cyclopropyl-2,3-dihydroxypropyl] imidazole-4-propionamide and (R)-α-(pivaloylmethyl)hydrocinnamic acid the (S)13 N—[(1S,2R,3S)-1-(cyclohexylmethyl)-3-cyclo-propyl-2,3-dihydroxypropyl]-α-[(R)-α-(3,3-dimethyl-2-oxobutyl) hydrocinnamamido]imidazole-4-propionamide as a solid, melting point 136° (from methylene chloride/methanol/ether/hexane);

from (S)-α-amino—N—[(1R,2S,3R)-1-(cyclohexylmethyl)-2,3-dihydroxy-4-methylpentyl]imidazole-4-propionamide and (S)-α-](t-butylsulphonyl) methyl]hydrocinnamic acid the (S)-α-[(S)-α-[(t-butylsuphonyl)-methyl]hydrocinnamamido]—N—[(1R,2R,3R)-1-(cyclohexylmethyl)-2,3-dihydroxy-4-methylpentyl]imidazole-4-propionamide as a white solid, melting point 114° (dec.; from methylene chloride/ether);

from (S)-α-amino—N—[(1S,2R,3S)-3-cyclohexyl-1-(cylohexylmethyl)-2,3-dihydroxypropyl]imidazole-4-propionamide and (S)-α-[(t-butylsulphonyl)methyl]hydrocinnamic acid the (S)-α-[(S)-α-[(t-butylsulphonyl)methyl]hydrocinnamamido]—N—[(1S,2R,3S)-3-cyclohexyl-1-(cyclohexylmethyl)-2,3-dihydroxypropyl]imidazole-4-propionamide as a white solid, MS: 673 (M+H)+.

from (S)-α-amino—N—[(1R,2S,3R)-3-cyclohexyl-1-(cyclohexylmethyl)-2,3-dihydroxypropyl]imidazole-4-propionamide and (S)-α-[(t-butylsulphonyl)methyl]hydrocinnamic acid the (S)-α-[(S)-α-[(t-butylsulphonyl)methyl]hydrocinnamamido]—N—[(1R,2S,3R)-3-cyclohexyl-1-(cyclohexylmethyl)-2,3-dihydroxypropyl]imidazole-4-propionamide as a white solid, MS: 673 (M+H)+.

from (S)-α-amino—N—[(1S,2R,3R,4RS)-1-(cyclohexylmethyl)-2,3-dihydroxy-4-methylhexyl]imidazole-4-propionamide and (S)-α-[(t-butylsulphonyl)methyl]hydrocinnamic acid the (S)-α-[(S)-α-[(t-butylsulphonyl)methyl]hydrocinnamamido] —N—[(1S,2R,3S,4RS )-1-(cyclohexylmethyl)-2,3-dihydroxy-4-methylhexyl]imidazole-4-propionamide as a white solid, MS: 647 (M+H)+.

from (S)-α-amino—N—[(1S,2R,3S,4RS)-1-(cyclohexylmethyl)-2,3-dihydroxy-4-methylhexyl]imidazole-4-propionamide and (S)-α-[(t-butylsulphonyl)methyl]hydrocinnamic acid the (S)-α-[(S)-α-[(t-butylsulphonyl)methyl]hydrocinnamamido]—N—[(1S,2R,3R,4RS)-1-(cyclohexylmethyl)-2, 3-dihydroxy-4-methylhexyl]imidazole-4-propionamide as a white solid, MS: 647 (M+H)+.

from (S)-α-amino—N—[(1S,2R,3S)-1-(cyclohexylmethyl)-2,3-dihydroxy-4-methylpentyl]hexanamide and (S)-α-[(t-butylsulphonyl)methyl]hydrocinnamic acid the (S)-α-[(t-butylsulphonyl)methyl]-N-[(S)-1-[[(1S,2R,3S)-1-(cyclohexylmethyl)-2,3-dihydroxy-4-methylpentyl]-carbamoyl]pentyl]hydrocinnamamide as a white solid, melting point 190° (from methylene chloride/ether/hexane);

from (S)-α-amino—N—[(1R,2S,3R)-1-(cyclohexylmethyl)-2,3-dihydroxy-4-methylpentyl]hexanamide and (S)-α-[(t-butylsulphonyl)methyl]hydrocinnamic acid the (S)-α-[(t-butylsulphonyl)methyl]—N—[(S)-1-[[(1R,2S,3S)-1-(cyclohexylmethyl)-2,3-dihydroxy-4-methylpentyl]-carbamoyl]pentyl]hydrocinnamamide as a white solid, melting point 182° (from methylene chloride/ether/hexane);

from (S)-α-amino—N—[(1S,2R,3S)-1-(cyclohexylmethyl)-3-cyclopropyl-2,3-dihydroxypropyl]imidazole-4-propionamide and (S)-α-[(t-butylsulphonyl)methyl]-hydrocinnamic acid the (S)-α-[(S)-α-[(t-butylsulphonyl)-methyl]hydrocinnamamido]—N—[(1S,2R,3S)-1-(cyclohexylmethyl)-3-cyclopropyl-2,3-dihydroxypropyl]imidazole-4-propionamide as a white solid, melting point 100 ° (dec.; from methylene chloride/ether/hexane);

from (S)-α-amino—N—[(1R,2S,3R)-1-(cyclohexylmethyl)-3-cyclopropyl-2,3-dihydroxypropyl]imidazole-4-propionamide and (S)-60 -[(t-butylsulphonyl)methyl]hydrocinnamic acid the (S)-60 -[(S)-α-[(t-butylsulphonyl)methyl]hydrocinnamamido]—N—[(1R,2S,3R)-1-(cyclohexylmethyl)-3-cyclopropyl-2,3-dihydroxypropyl]imidazole-4-propionamide as a white solid, melting point 100° (dec.; from methylene chloride/ether/hexane);

from (S)-α-amino—N—[(1S,2R,3S)-3-cyclohexyl-1-(cyclohexylmethyl)-2,3-dihydroxypropyl]hexanamide and (S)-α-[(t-butylsulphonyl)methyl]hydrocinnamic acid the (S)-α-[(t-butylsulphonyl)methyl]—N—[(S)-1-[[(1S,2R,3S)-3-cyclohexyl-1-(cyclohexylmethyl)-2,3-dihydroxypropyl]carbamoyl]pentyl]hydrocinnamamide as a white solid, melting point 187° (from methylene chloride/ether/hexane);

from (S)-α-amino—N—[(1R,2S,3R)-3-cyclohexyl-1-(cyclohexylmethyl)-2,3-dihydroxypropyl]hexanamide and (S)-α-[(t-butylsulphonyl)methyl]hydrocinnamic acid the (S)-α-[(t-butylsulphonyl)methyl]—N—[(S)-1-[[(1R,2S,3R)-3-cyclohexyl-1-(cyclohexylmethyl)-2,3-dihydroxypropyl]carbamoyl]pentyl]hydrocinnamamide as a white solid, melting point 187° (from methylene chloride/ether/hexane);

from (S)-α-amino—N—[(1S,2R,3S)-1-(cyclohexylmethyl-2,3-dihydroxy-4-methylpentyl]imidazole-4-propionamide and (S)-α-[(diethoxyphosphinyl)methyl]hydrocinnamic acid (see EPA 0 117 429) the diethyl[(S)-2-[[(S)-1-[[(1S,2R,3S)-1-(cyclohexylmethyl)-2,3-dihydroxy-4-methylpentyl]carbamoyl]-2 -imidazol-4-ylethyl]carbamoyl]-3-phenylpropyl]phosphonate as a white solid, melting point 98° (from methylene chloride/ether/hexane);

from (S)-α-amino—N—[(1S,2R,3S)-1-(cyclohexylmethyl)-2,3 -dihydroxy-4-methylpentyl]imidazole-4-propionamide and dibenzylacetic acid the (S)—N—[(1S,2R,3S)-1-(cyclohexylmethyl)-2,3-dihydroxy-4-methylpentyl]-α-(2,2-dibenzylacetamido) imidazole-4-propionamide as a white solid, melting point 193° (from methylene chloride/ methanol/ether/hexane).

from (S)-α-amino—N—[(1S,2R,3S)-1-(cyclohexylmethyl)-2,3-dihydroxy-4-methylpentyl]imidazole-4-propionamide and (RS)-α-[(t-butylsulphonyl)methyl]-m-methoxyhydrocinnamic acid the (S)-α-[(R or S)-α-[(t-butylsulphonyl)methyl]-m-methoxyhydrocinnamamido]—N—[(1S,2R,3S)-1-(cyclohexylmethyl)-2,3-dihydroxy-4-methylpentyl]imidazole-4-propionamide as a white solid, melting point 153° (from methylene chloride/ether/hexane), and the epimeric (S)-α-[(S or R)-α-[t-butylsulphonyl)methyl]-m-methoxyhydrocinnamamido]—N—[(1S,2R,3S)-1-(cyclohexylmethyl)-2,3-dihydroxy-4-methylpentyl]imidazole-4-propionamide as a white solid, melting point 108° (from methylene chloride/ether/hexane);

from (S)-α-amino-N-[(1S,2R,3S)-1-(cyclohexylmethyl)-2,3-dihydroxy-4-methylpentyl]imidazole-4-propionamide and (RS)-α-[(t-butylsulphonyl)methyl]-p-methoxyhydrocinnamic acid the (S)-α-[(R or S)-α-[(t-butylsulphonyl)methyl]-p-methoxyhydrocinnamamido]—N—[(1S,2R,3S) -1-(cyclohexylmethyl)-2,3-dihydroxy-4-methylpentyl]-imidazole-4-propionamide as a white solid, melting point 121° (from methylene chloride/ether/hexane), and the epimeric (S)-α-[(S or R)-α-[t-butylsulphonyl)methyl]-p-methoxyhydrocinnamamido]—N—[(1S,2R,3S)-1-(cyclohexylmethyl)-2,3-dihydroxy-4-methylpentyl]imidazole-4-propionamide as a white solid, melting point 109° (from methylene chloride/methanol/ether/hexane);

from (S)-α-amino—N—[(1S,2R,3S)-1-(cyclohexylmethyl)-2,3-dihydroxy-4-methylpentyl]imidazole-4-propionamide and (S)-α-[[(RS)-t-butylsulphinyl)methyl]hydrocinnamic acid the (S)-α-[(S)-α-[[(RS)-t-butylsulphinyl]methyl]hydrocinnamamido]—N—[(1S,2R,3S)-1-(cyclohexylmethyl)-2,3-dihydroxy-4-methylpentyl]imidazole-4-propionamide as a white solid, melting point 100° (dec.; from methylene chloride/ether/hexane);

from (S)-α-amino—N—[(1S,2R,3S)-1-(cyclohexylmethyl)-2,3-dihydroxy-4-methylpentyl]imidazole-4-propionamide and (2R,3R or S)-2-benzyl-3-hydroxy-5,5-dimethyl-4-oxohexanoic acid the (s)—N—[(1S, 2R,3S)-1-(cyclohexylmethyl)-2,3-dihydroxy-4-methylpentyl]-α-[(R)-α-[(R or S)-1-hydroxy-2,3-dimethyl-2-oxobutyl]hydrocinnamamido]imidazole-4-propionamide as a white solid, melting point 100° (dec.; from methylene chloride/ether/hexane);

from (S)-α-amino—N—[(1S,2R,3S)-1-(cyclohexylmethyl)-2,3-dihydroxy-4-methylpentyl]imidazole-4-propionamide and (2R,3S or R)-2-benzyl-3-hydroxy-5,5-dimethyl-4-oxohexanoic acid the (S)—N—[(1S,2R,3S-1-(cyclohexylmethyl)-2,3-dihydroxy-4-methylpentyl]-α-[(R)-α-[(S or R)-1-hydroxy-2,3-dimethyl-2-oxobutyl]hydrocinnamamido]imidazole-4-propionamide as a while solid, melting point 100° (dec.; from methylene chloride/ether/hexane);

from (S)-α-amino—N—[(1S,2R,3S)-1-(cyclohexylmethyl)-3- cyclobutyl-2,3-dihydroxypropyl]imidazole-4-propionamide and (S)-α-[(t-butylsulphonyl)methyl]-hydrocinnamic acid the (S)-α-[(S)-α-8 (t-butylsulphonyl)methyl]hydrocinnamamido]—N—(1S,2R,3S)-3-cyclobutyl-1-(cyclohexylmethyl)-2,3-dihydroxypropyl]imidazole-4-propionamide as a white solid, melting point 110° (dec.; from methylene chloride/methanol/ether/hexane);

from (S)—N—[(1S, 2R,3S)-1-(cyclohexylmethyl)-2,3-dihydroxy-4-methylpentyl]-α-[(3-pheynl-L-alanyl-)amino]imidazole-4-propionamide and 3-(3-pyridyl)propionic acid the (S)—N—[(1S,2R,3S)-1-(cyclohexylmethyl)-2,3-dihydroxy-4-methylpentyl]-α-[(S)-α-(3-pyridinepropionamido)hydrocinnamamido]imidazole-4-propionamide as a white solid, melting point 120° (from methylene chloride/ether/ hexane);

from (S)—N—[(1S,2R,3S)-1-(cyclohexylmethyl-2,3-dihydroxy-4-methylpentyl]-α-[(3-phenyl-L-alanyl-)amino]imidazole- 4-propionamide and 2-(2-pyridyl)benzoic acid the (S)—N—[(1S,2R,3S)-1-(cyclohexylmethyl)-2,3-dihydroxy-4-methylpentyl]-α-[(S)-α-[2-(2-pyridyl)benzamido]hydrocinnamamido]imidazole-4-propionamide as a white solid, melting point 125° (from methylene chloride/ether/hexane);

from (S)-α-amino—N—[(1S,2R,3S)-1-(cyclohexylmethyl)-3-cyclopropyl-2,3-dihydroxypropyl]imidazole-4-propionamide and 2-(RS)-benzyl-3-morpholinocarbonylpropionic acid the (S)—N—[(1S,2R,3S)-1-(cyclohexylmethyl)-3-cyclopropyl-2,3-dihydroxypropyl-α-[(R)-α-[(morpholinocarbonyl) methyl]hydrocinnamamido]imidazole-4-propionamide, MS: 624 (M+H)+, and the epimeric (S)—N—][(1S,2R,3S)-1-(cyclohexylmethyl)-3-cyclopropyl-2,3-dihydroxypropyl]-α-[(S)-α-[(morpholinocarbonyl)methyl]hydrocinnamamido]imidazole-4-propionamide, MS: 624 (M+H)+;

from (S)-α-amino—N—[(1S,2R,3S)-1-(cyclohexylmethyl)-3-cyclopropyl-2,3-dihydroxypropyl]imidazole-4-propionamide and (RS)-[(t-butylsulphonyl)methyl]-1-naphthalenepropionic acid the (S)-α-[(R)-α-[(t-butylsulphonyl) methyl]-1-naphthalenepropionamido]—N—[(1S,2R,3S)-1-(cyclohexylmethyl)-3-cyclopropyl-2,3-dihydroxypropyl]imidazole-4-propionamide as a foam, MS: 681 (M+H)+, and the epimeric (S)-α-[(S)-α-[(t-butylsulphonyl)methyl]-1-naphthaleneptopionamido]—N—[(1S,2R,3S)- 1-(cyclohexylmethyl)-3-cyclopropyl-2,3-dihydroxypropyl-]imidazole-4-propionamide in the form of a foam, MS: 681 (M+H)+;

from (S)-α-amino—N—[(1S,2R,3S)-1-(cyclohexylmethyl)-3-cyclopropyl-2,3-dihydroxypropyl]imidazole-4-propionamide and (RS)-[(t-butylsulphonyl)-4-phenylbutyric acid the (S)-α-[(S)-2-[(t-butylsulphonyl)methyl]-4-phenylbutyramido]—N—[(1S,2R,3S)-1-(cyclohexylmethyl)-3-cyclopropyl-2,3-dihydroxypropyl-]imidazole-4-propionamide in the form of a foam, MS: 645 (M+H)+, and the epimeric (S)-α-[(R)-2-[(t-butylsulphonyl)methyl]-4-phenylbutyr- amido]-N-[(1S, 2R, 3S )-1-(cyclohexylmethyl)-3-cyclopropyl-2,3-dihydroxypropyl]imidazole-4-propionamide as a foam, MS: 645 (M+H)+;

from (S)-α-amino-N-[(1S, 2R, 3S)-1-(cyclohexylmethyl) -3-cyclopropyl-2,3-dihydroxypropyl]imidazole-2-propionamide and (S)-α-(t-butylsulphonyl)methyl]hydrocinnamic acid the (S)-α-[(R)-α-[(t-butylsulphonyl)methyl]hydrocinnamamido]-N-[(1S, 2R, 3S)-1-(cyclohexylmethyl)-3-cyclopropyl-2,3-dihydroxypropyl]imidazole-2-propionamide as an amorphous solid, MS: 631 (M+H)+.

The propionamides used as the starting materials were prepared as follows:

(S)-α-Amino-N-[(1S, 2R, 3S)-1-(cyclohexylmethyl)-2,3-dihydroxy-4-methylpentyllimidazole-4-propionamide and (S)-α-amino-N-[(1R, 2S, 3R)-1-(cyclohexylmethyl)-2,3-dihydroxy-4-methylpentyllimidazole-4-propionamide 4.0 g (100 mmol) of a 60% sodium hydride dispersion in oil are suspended in 70 ml of dimethyl sulphoxide and 350 ml of tetrahydrofuran and treated at 3° with 21.8 ml (104 mmol) of hexamethyldisilazane. After stirring for 1 hour the reaction mixture is treated dropwise within 30 minutes with a suspension of 41.75 g (104 mmol) of triphenylisobutylphosphonium bromide (prepared by boiling equimolar amounts of triphenylphosphine and isobutyl bromide in toluene for 2 days) in 250 ml of tetrahydrofuran. The reaction mixture is stirred at room temperature for 1 hour, then cooled to −70° and treated dropwise within 45 minutes with a solution of 23 g (90 mmol) of t-butoxycarbonylamino-(3S)-cyclohexylpropylaldehyde. Then, the reaction mixture is allowed to warm slowly to room temperature overnight while stirring. Thereafter, firstly 10 ml of methanol and then 500 ml of saturated sodium potassium tartrate solution are added. The reaction mixture is poured on to ice and extracted three times with ethyl acetate. The organic phases are washed with water and 2N sodium bicarbonate solution, dried and evaporated. Chromatography of the crude product (39.6 g) for purification on a kilogram of silica gel using an 85:15 mixture of hexane and ether yields 13.82 g of t-butyl [(SR,Z)-1-(cyclohexylmethyl)-4-methyl-2-pentenyl]carbamate as an oil. Crystallization from hexane yields a white solid which melts at 74°, MS: 296 (M+H)+.

16 g (54.1 mmol) of the above compound, 21.96 g (162 mmol) of 4-methylmorpholine-4-oxide monohydrate, 10 ml of a solution of 1 g of osmium tetroxide in 199 ml of t-butanol and 1 ml of 70% t-butyl hydroperoxide in 100 ml of tetrahydrofuran are stirred at room temperature overnight. Thereafter, 50 ml of a 38% sodium bisulphite solution are added, the reaction mixture is stirred at room temperature for 1 hour, poured on to ice and thereafter extracted with ether. The organic phases are washed in succession with saturated ammonium chloride solution, 2M sodium bicarbonate solution and water. After drying, filtration and evaporation of the organic solution the residue (18.7 g), for purification, was chromatographed on 1 kg of silica gel using a 7:3 mixture of hexane and ether as the eluting agent. The component which runs more rapidly (Rf value 0.5 in a 1:1 mixture of hexane and ether) is t-butyl [(1SR,2SR,3SR)-1-(cyclohexylmethyl)-2,3-dihydroxy-4-methylpentyl]carbamate. In this manner there are obtained 7.52 g of this compound as a white foam, MS: 330 (M+H)+.

This compound was converted in an analogous manner to that described in Example 1 by cleavage of the Boc protecting group with hydrochloric acid in dioxan, reaction with (Fmoc)₂His-OH, cleavage of the two protecting groups with piperidine and chromatographic separation of the two isomers into (S)-α-amino-N-[(1S,2R,3S)-1-(cyclohexylmethyl)-2,3-dihydroxy-4-methylpentyl]imidazole-4-propionamide and (S)-α-amino-N-[(1R,2S,3R)-1-(cyclohexylmethyl)-2,3-dihydroxy-4-methylpentyl]imidazole-4-propionamide.

The following propionamides were prepared in an analogous manner to that described above:

(S)-α-Amino-N-[(1S,2R,3S)-3-cyclohexyl-1-(cyclohexylmethyl)-2,3-dihydroxypropyl]imidazole-4-propionamide and the diastereomeric (S)-α-amino-N-[(1R,2S,3R)-3-cyclohexyl-1-(cyclohexylmethyl)-2,3-dihydroxypropyl]-imidazole-4-propionamide using cyclohexylmethyl bromide in place of isobutyl bromide for the preparation of the Wittig reagent;

(S)-α-amino-N-[(1S,2R,3S)-1-(cyclohexylmethyl)-3-cyclopropyl-2,3-dihydroxypropyl]imidazole-4-propionamide and the diastereomeric (S)-α-amino-N-[(1R,2S,3R)-1-(cyclohexylmethyl)-3-cyclopropyl-2,3-dihydroxyproxypropyl]-imidazole-4-propionamide using cyclopropylmethyl bromide in place of isobutyl bromide for the preparation of the Wittig reagent;

(S)-α-amino-N-[(1S,2R,3S)-1-(cyclohexylmethyl)-2,3-dihydroxy-4-methylpentyl]hexanamide and the diastereomeric (S)-α-amino-N-[(1R,2S,3R)-1-(cyclohexylmethyl)-2,3-dihydroxy-4-methylpentyl]hexanamide using (Fmoc)$_2$Nle-OH in place of (Fmoc)$_2$His-OH;

(S)-α-amino-N-[(1S,2R,3S)-3-cyclohexyl-1-(cyclohexylmethyl)-2,3-dihydroxypropyl]hexanamide and the diastereomeric (S)-α-amino-N-[(1R,2S,3R)-3-cyclohexyl-1-(cyclohexylmethyl)-2,3-dihydroxypropyl]hexanamide using cyclohexylmethyl bromide in place of isobutyl bromide for the preparation of the Wittig reagent and (Fmoc)$_2$Nle-OH in place of (Fmoc)$_2$His-OH;

(S)-α-amino-N-[(1S,2R,2S)-1-(cyclohexylmethyl)-3-cyclopropyl-2,3-dihydroxypropyl]imidazole-2-propionamide using cyclopropylmethyl bromide in place of isobutyl bromide for the preparation of the Wittig reagent, using (Boc)$_2$-iso-His-OH (see U.S. Pat. No. 4,612,324) in place of (Fmoc)$_2$His-OH and using a 1:1 mixture of trifluoroacetic acid and methylene chloride in place of piperidine for the cleavage of the two protecting groups.

(S)-α-Amino-N-[(1S,2R,3S,4RS)-1-(cyclohexylmethyl)-2,3-dihydroxy-4-methylhexyl]imidazole-4-propionamide and the diastereomeric (S)-α-amino-N-[(1R,2S,3R,4RS)-1-(cyclohexylmethyl)-2,3-dihydroxy-4-methylhexyl]imidazole-4-propionamide These compounds were obtained in an analogous manner to that described in Example 3 by reacting 3-t-butyl 5-methyl (4S,5R)-4)(cyclohexylmethyl)-2,2-dimethyl-3,5-oxazolidinedicarboxylate with sec-butyllithium, reduction with sodium borohydride, chromatographic separation of the resulting isomers, cleavage of the Boc protecting group with methanolic hydrochloric acid, coupling with (Fmoc)$_2$His-OH and cleavage of the two protecting groups with piperidine.

(S)-α-Amino-N-(1S,2R,3S)-1-(cyclohexylmethyl)-3-cyclobutyl-2,3-dihydroxypropyl]imidazole-4-propionamide A solution of 7.23 g (22.2 mmol) of t-butyl (4S,5R)-4-(cyclohexylmethyl)-5-formyl-2,2-dimethyl-3-oxazolidinecarboxylate in 150 ml of tetrahydrofuran is added dropwise within 40 minutes at 30° to a solution of the Grignard compound prepared from 15 g (111 mmol) of bromocyclobutane and 2.7 g (111 mgram atom) of magnesium shavings in 150 ml of tetrahydrofuran and the reaction mixture is subsequently stirred at room temperature overnight. Thereafter, the reaction mixture is poured into 300 ml of a saturated ammonium chloride solution and extracted three times with 600 ml of ether each time. The ether extracts are washed with ammonium chloride solution, dried, filtered and evaporated. The crude product (9.34 g) is chromatographed on 500 g of silica gel with a 92.5:7.5 mixture of toluene and ethyl acetate as the eluting agent, whereby there are obtained 2.44 g of t-butyl (4S,5R)-4-(cyclohexylmethyl)-5-](S)-cyclobutylhydroxymethyl]-2,2-diemthyl-3-oxazolidinecarboxylate as an oil, MS: 381 (M)+, and 2.9 g of the opimeric compound t-butyl (4S,5R)-4-(cyclohexylmethyl)-5-[(R)-cyclobutylhydroxymethyl]-2,2-dimethyl-3-oxazolidinecarboxylate, likewise as an oil, MS: 381 (M)+.

The acids used as the starting materials are known or were prepared as folows:

(RS)-α-[(t-Butylsulphonyl)methyl-p-methoxyhydrocinnamic acid

A mixture of 3.16 g (16.4mmol) of 2-(p-methoxybenzyl)acrylic acid and 1.85 ml (16.4 mmol) of t-butyl mercaptan in 10 ml of ethanol is treated dropwise while cooling with ice with 30.4 ml of a 1.08N sodium ethylate/ethanol solution. Thereafter, the reaction mixture is stirred at room temperature for 1 hour, whereby a solid separates. Subsequently, 30.4 ml of 2.5N hydrochloric acid in dioxan are added while cooling with ice and the mixture is stirred at room temperature for a further 30 minutes. Thereafter, the reaction mixture is evaporated under reduced pressure and the crude (RS)-α-[(t-butylthio)-methyl[-p-methoxyhdrocinnamic acid obtained is thereafter suspended in 200 ml of methylene chloride. The suspension is treated portionwise with 5.66 g (32.8 mmol) of 3-chloroperbenzoic acid while cooling with ice and then stirred at room temperature overnight. Then, the reaction mixture is washed in succession with 10% potassium iodide solution and water, dried over sodium sulphate and evaporated under reduced pressure. The residue is triturated with ether, the solid is filtered off and the ethereal phase is evaporated under reduced pressure. For purification, the residue is chromatographed on silica gel with a 5:4:1 mixture of hexane, ethyl acetate and methanol as the eluting agent, whereby there are obtained 3.3 g of (RS)-α-[(t-butylsulphonyl)methyl]-p-methoxyhydrocinnamic acid as a yellowish solid, MS: 314 (M)+.

The (RS)-α-[(t-butylsulphonyl)methyl]-m-methoxyhydrocinnamic acid was prepared starting from 2-(m-methoxybenzyl)acrylic acid in an analogous manner to that described above.

(S)-α-[[(RS)-t-Butylsulphinyl]methyl]hydrocinnamic acid 550 ml of water are placed in a sulphonation flask having a mechanical stirrer, pH control as well as a dropping funnel and treated while stirring vigorously with 4.85 g (16.36 mmol) of ethyl (RS)-α-[[(RS)-t-butylsulphinyl]methyl]hydrocinnamate (see EPA 0 236 734) in 15 ml of dimethyl sulphoxide. The reaction solution is thereafter adjusted to pH 7.5, treated with 200 mg of α-chymotrypsin and the pH is held constant with 0.037N calcium hydroxide solution. After 220 ml of this calcium hydroxide solution have been consumed (about 45 hours) the unreacted ester is extracted with ethyl acetate, the aqueous phase is adjusted to pH 2 with 30% sulphuric acid and extracted with ethyl acetate. The extracts are washed in succession with water and saturated sodium chloride solution, dried over magnesium sulphate and evaporated, whereby there are obtained 2.50 g of (S)-α-[[(RS)-t-butylsulphinyl]hydrocinnamic acid, MS: 269 (M+H)$^{30}$.

(2R,3R or S)-2-Benzyl-3-hydroxy-5,5-dimethyl-4-oxo-hexanoic acid 1.2 g of (R)-α-(pivaloylmethyl)hydrocinnamic acid in 50 ml of tetrahydrofuran are added dropwise at −70° under argon to 6.5 ml of a 1.6M solution of n-butyllithium in hexane. After stirring for 30 minutes 6 g of molybdenum peroxide [MoO5.pyridine.HMPA; E. Vedejes et al., J. Org. Che., 43, 188 (1978)] are added by means of a powder funnel. Thereafter, the temperature is allowed to rise to −15° within 30 minutes and the reaction mixture is treated with 50 ml of saturated sodium sulphite solution. Subsequently, the reaction mixture is allowed to warm to room temperature and is extracted with ether. The ether phase is washed in succession with water and sodium chloride solution, dried over sodium sulphate and evaporated under reduced pressure. The oily residue (1 g) is reacted with ethereal diazomethane solution. After evaporation of the reaction solution the purification and separation of the two diastereomeric esters is effected by chromatography on silica gel using a 4:1 mixture of hexane and ether. In this manner there are obtained 325 mg of the less polar methyl (2R,3R or S)-2-benzyl-3-hydroxy-5,5-dimethyl-4-oxohexanoate and 225 mg of the more polar methyl (2R,3S or R)-2-benzyl-3-hydroxy-5,5-dimethyl-4-oxohexanoate in the form of colourless solids.

A mixture of 300 mg (1.07 mmol) of the less polar (2R,3R or S)-2-benzyl-3-hydroxy-5,5-dimethyl-4-oxohexanoate and 1.07 ml of 1N sodium hydroxide solution in 10 ml of methanol is stirred at room temperature for 3 hours. Thereafter, the reaction mixture is neutralized with 1.07 ml of 1N hydrochloric acid and evaporated under reduced pressure. The residue is triturated with ethyl acetate and the insoluble solid is separated. After evaporation of the ethyl acetate phase there are obtained 180 mg of (2R,3R or S)-2-benzyl-3-hydroxy-5,5-dimethyl-4-oxohexanoic acid as a colourless solid, MS: 231 (M-CH3-H2O)+.

In an analogous manner, from methyl (2R,3S or R)-2-benzyl-3-hydroxy-5,5-dimethyl-4-oxohexanoate there was obtained the epimeric (2R, 3S or R)-2-benzyl-3-hydroxy-5,5-dimethyl-4-oxohexanoic acid, MS: 231 (M-CH3-H2O)+.

2-(RS)-benzyl-3-morpholinocarbonylpropionic acid 1.0 g (4.2 mmol) of 3-ethoxycarbonyl-4-phenylbutyric acid is dissolved in 25 ml of dimethylformamide and treated with 0.37 g (4.2 mmol) of morpholine, 0.81 g (4.2 mmol) of EDC and 1.3 g (8.4 mmol) of HOBT and stirred at room temperature for 48 hours. Thereafter, the reaction solution is evaporated in a high vacuum, and the residue is dissolved in ethyl acetate and washed in succession with water, saturated sodium bicarbonate solution and saturated sodium chloride solution. Then, the organic phase is dried over sodium sulphate and evaporated under reduced pressure, and the residue is chromatographed on silica gel using a 95:5 mixture of methylene chloride and ethanol, whereby there is obtained ethyl 2-(RS)-1-benzyl-3-morpholinocarbonylpropionate as a colourless oil, MS: 305 (M)+.

0.42 g (1.4 mmol) of the above ester are dissolved in 2 ml of ethanol and treated with 2.1 ml (1.5 mol equivalents) of 1N sodium hydroxide solution. The reaction solution is then stirred at 50° for 4 hours and the residue is dissolved in water and washed with ether. The aqueous phase is acidified with 2.3 ml of 1N hydrochloric acid and extracted with methylene chloride. The organic extracts are dried over sodium sulphate and evaporated under reduced pressure, whereby there is obtained 2-(RS)-benzyl-3-morpholinocarbonylpropionic acid as a colourless oil which is used directly in the next step, MS: 277 (M)+.

(RS) -t-Butylsulphonylmethyl-1-naphthalenemodionic acid and (RS)-t-butysuldhonyl-4-phenylbutyric acid These compounds were prepared in analogy to the synthesis of (RS)-α-[(t-butylsulphonyl)methyl]hydrocinnamic acid described in EPA 0.236.734 starting from diethyl 1-naphthylmalonate and diethyl phenylethylmalonate, respectively. The two compounds have the following mass spectra: (RS)-[(t-Butylsulphonyl)methyl]-1-naphthalenepropionic acid, MS: 334 (M)+, and (RS)-(t-butylsulphonyl)-4-phenylbutyric acid, MS: 298 (M)+.

EXAMPLE 5

50 mg of (S)-α-[(S)-α-[(t-butylsulphonyl)methyl]hydrocinnamido]-N-[(1S,2R,3S)-1-(cyclohexylmethyl)-2,3-dihydroxy-4-methylpentyl]imidazole-4-propionamide and 50 mg of p-toluenesulphonic acid in 3 ml of dimethoxypropane are stirred at room temperature overnight. The reaction mixture is thereafter poured into 2N sodium bicarbonate solution and extracted with ethyl acetate. The organic phases are washed with water, dried and evaporated, whereby there is obtained (S)-α-[(S)-α-[(t-butylsulphonyl)methyl]hydrocinnamido]-N-[(S)-(cyclohexylmethyl)[(4R,5S)-5-isopropyl-2,2-dimethyl-1,3-dioxolan-4-yl]methyl]imidazole-4-propionamide as a solid, MS: 673 (M+H)+.

EXAMPLE 6

100 mg of (S)-α-[(S)-α[(t-butylsulphonyl)methyl]-hydrocinnamido]-N-[(1S,2R,3S)-1-(cyclohexylmethyl)-2,3-dihydroxy-4-methylpentyl]imidazole-4-propionamide and 60 mg of dimethylaminopyridine in 5 ml of pyridine and 0.2 ml of valeryl chloride are left to stand at room temperature overnight. Thereafter, the reaction mixiture is taken up in ethyl acetate and the organic phase is washed in succession with 2N sodium carbonate solution, 2N copper sulphate solution and water, dried and evaporated. Chromatography of the residue on 15 g of silica gel with a 200:10:1 mixture of methylene chloride, methanol and ammonia yields (1R,2S)-1-[(S)-1-[(S)-α-[(t-butylsulphonyl)methyl]hydrocinnamamido]imidazole-4-propionamido]-2-cyclohexylethyl]-2-isopropylethylene divalerate as a foam, MS: 802 (M+H)+, and (1S,2R,3S)- 3-[(S)-α-[(S)-α-[(t-butylsulphonyl)methyl[hydrocinnamamido]imidazole-4-propionamide]-4-cyclohexyl-2-hydroxyl-1-isopropylbutyl valerate as an oil, MS: 717 (M+H)+.

EXAMPLE 7

100 mg of (S)-α-[(S)-α[(t-butylsulphonyl)methyl]-hydrocinnamamido]-N-[(1S,2R,3S)-1-(cyclohexylmethyl)-2,3-dihydroxy-4-methylpentyl]imidazole-4-propionamide, 200 mg of succinic anhydride and 200 mg of sodium carbonate in 10 ml of dimethylformamide are stirred at 50° overnight. Thereafter, the reaction mixture is taken up in ethyl acetate and the organic phase is washed with saturated ammonium chloride solution and water, dried and evaporated. Chromatography of the resiude on 20 g of silica gel with a 90:10:1:0.5 mixture of methylene chloride, methanol, water and acetic acid yields (1S,2R,3S)-3-[(S)-α-[(t-butylsulphonyl)methyl]-hydrocinnamamido]imidazole-4-propionamido]-4-cyclohexyl-1-isopropylbutyl hydrogen succiate as a foam, MS: 733 (M+H)+, and (1R,2S)-1-[(S)-1-[(S)-α-[(t-butylsulphonyl)methyl]hydrocin-namamido]imidazole-4-propionamide]-2-cyclohexyle-thyl]-2-isopropylethylene bis(hydrogen succinate) in the form of a foam, MS: 833 (M+H)+.

EXAMPLE 8

214 mg of (S)-α-[(S)-α-[(t-butylsulphonyl)methyl]-hydrocinnamamido]-N-[(1S,2R,3S)-1-(cyclohexylme-thyl)-2,3-dihydroxy-4-methylpentyl]imidazole-4-propionamide in 5 ml of pyridine and 5 ml of acetic anhydride are heated to 90° for 2 hours and thereafter evaporated, whereby there is obtained as the residue (1R,2S)-1-[(S)-1-[(S)-α-[(S)-α-[(t-butylsulphonyl)methyl]hy-drocinnamamido]imidazole-4-propionamido]-2-cyclohexylethyl]-2-isopropylethylene diacetate in the form of a foam, Rf value 0.2 in a 140:10:1 mixture of methylene chloride, methanol and ammonia.

EXAMPLE 9

100 mg of (S)-α-[(S)-α-[(t-butylsulphonyl)methyl]hy-drocinnamamido ]-N-[(1S, 2R, 3S) -1-(cyclohexylme-thyl)-2,3-dihydroxy-4-methylpentyl]imidazole-4-propionamide in 5 ml of pyridine, 2.5 ml of acetic anhydride and 2.5 ml of formic acid are heated to 90° for 2 hours. Evaporation of the solvent and chromatography on 20 g of silica gel with a 140:10:1 mixture of methylene chloride, methanol and ammonia yields (1R,2S)-1-[(S)-1-[(S)-α-[(S)-α-[(t-butylsulphonyl)methyl]hyrocin-namamido]imidazole-4-propionamido]-2-cyclohexyle-thyl]-2-isopropylethylene diformate as a white solid, MS: 689 (M+H)+.

EXAMPLE 10

A mixture of 1 ml of acetic anhydride and 1 ml of formic acid is added at 0° to 100 mg of (S)-α-[(S)-α-[(t-butylsulphonyl)methyl]hydrocinnamamido]-N-[(1S,2R,3S)-1-(cyclohexylmethyl)-2,3-dihydroxy-4-methylpentyl]-imidazole-4-propionamide in 2 ml of pyridine. The reaction mixture is left to stand at room temperature overnight and is thereafter evaporated on a rotary evaporator at a bath temperature of approximately 30°. The residue is dissolved in ether and the organic solution is washed in succession with 2N sodium bicarbonate solution, 2N copper sulphate solution and water, dried and evaporated, whereby there is obtained (1S,2R,3S)-3-[(S)-α-[(S)-α-[(t-butylsulphonyl)-methyl]hydrocinnamamido]imidazole-4-propionamido]-4-cyclohexyl-2-hydroxy-1-isopropylbutyl formate as a foam, MS: 661 (M+H)+.

EXAMPLE 11

130 mg of (S)-α-[(S)-α-[(t-butylsulphonyl)methyl]hy-drocinnamamido]-N-[(1S, 2R, 3S )-1-(cyclohexylme-thyl)-2,3-dihydroxy-4-methylpentyl]imidazole-4-propionamide and 130 mg of p-toluenesulphonic acid in 1 ml of trimethylacetaldehyde and 10 ml of methylene chloride are left to stand at room temperature for 24 hours. Thereafter, the reaction mixture is taken up in ether and the organic phase is washed in succession with 2N sodium bicarbonate solution and water, dried and evaporated. Chromatography of the residue on 30 g of silica gel using a 200:10:1 mixture of methylene chloride, methanol and ammonia yields (S)-N-[(S)-1-[(2R or S,4R,5S)-2-t-butyl-5-isopropyl-1,3-dioxolan-4-yl]-2-cyclohexylethyl]-α-[(S)-α-[(t-butylsulphonyl)methyl]-hydrocinnamamido]imidazole-4-propionamide as a foam, MS: 701 (M+H)+.

In an analogous manner to that described above, from (S)-α-[(S)-α-[(t-butylsulphonyl)methyl]hydrocin-namamido]-N-(1S,2R,3S)-1-(cyclohexylmethyl)-3-cyclopropyl-2,3-dihydroxypropyl]imidazole-4-propionamide and trimethylacetaldehyde there was prepared (S)-N-[(S)-1-[(4R,5S)-2-t-butyl-5-cyclopropyl-1,3-dioxolan-4-yl]-2-cyclohexylethyl]-α-[(S)-α-[(t-butylsulphonyl)methyl]hydrocinnamamido]imidazole-4-propionamide, MS: 699 (M+H)+.

EXAMPLE 12

100 mg of (S)-α-[(S)-α-[(t-butylsulphonyl)methyl]hy-drocinnamamido]-N-[(1S,2R,3S)-1-(cyclohexylmethyl)-2,3-dihydroxy-4-met hylpentyl]imidazole-4-propionamide in 2 ml of pyridine are treated at 0° with 0.2 ml of methoxyacetyl chloride and left to stand at room temperature overnight. Evaporation of t he reaction mixture and chromatography of the residue on 20 g of silica gel with a 140:10:1 mixture of methylene chloride, methanol and ammonia yields (1S,2R)-[(S)-1-[(S)-α-[(S)-α-[(t-butylsulphonyl)methyl]hydrocin-namamido]imidazole-4-propionamido]-2-cyclohexyle-thyl]-1-isopropylethylene bis(methoxyacetate) as a foam, MS: 777 (M+H)+.

In an analogous manner to that described above, from (S)-α-[(S)-α-[(t-butylsulphonyl)methyl]hydrocin-namamido]-N-[(1S,2R,3S)-1-(cyclohexylmethyl)-3-cyclopropyl-2,3-dihydroxypropyl]imidazole-4-propionamide and methoxyacetyl chloride there was prepared (1R,2S)-1-[(S)-1-[[N-[(S)-α-[(t-butylsulphonyl)-methyl]cinnamoyl]-L-histidyl]amino]-2-cyclohexyle-thyl]-2-cyclopropylethylene bis-(methoxyacetate), MS: 755 (M+H)+.

EXAMPLE 13

A mixture of 100 mg (0.37 mmol) of (1S or R,2R,3S)-3-amino-4-cyclohexyl-1-(1-cyclohexen-1-yl)-1,2-butanediol and 257 mg (0.41 mmol) of N-[(S)-α-[(t-butylsulphonyl)methyl]hydrocinnamoyl]-3-(2,4-dinitro-phenyl)-L-histidine in 15 ml of acetonitrile is treated under argon in succession at room temperature with 83 mg (0.82 mmol) of triethylamine, 67 mg (0.41 mmol) of HOBT and 168 mg (0.41 mmol) of HBTU and the reaction mixture is thereafter stirred at room temperature for 3 hours. For the working-up, the reaction mixture is concentrated under reduced pressure to about ¼ of the original volume, then diluted with 50 ml of ethyl acetate and washed in succession with water, saturated sodium bicarbonate solution, water and saturated sodium chloride solution. The organic phase is dried over sodium sulphate and evaporated under reduced pressure, and the residue is chromatographed on silica gel with a 98:2 mixture of methylene chloride and methanol as the eluting agent, whereby there are obtained 140 mg (0.17 mmol) of (S)-α-[(S)-α-[(t-butylsulphonyl)methyl]hy-drocinnamido]-N-[(1S,2R,3S or R)-1-(cyclohexylme-thyl)-3-(1-cyclohexen-1-yl)-2,3-dihydroxypropyl]-1-(2,4-dinitrophenyl)imidazol-4-propionamide in the form of a yellow foam, MS: 838 (M+H)+. This is dissolved in 3 ml of dimethylformamide and stirred at room temperature for 3 hours with 0.15 ml (1.7 mmol) of thiolac-tic acid. Thereafter, the reaction solution is evaporated in a high vacuum, the residue is dissolved in 15 ml of ethyl acetate and the reaction solution is washed in succession with saturated sodium carbonate solution, water and saturated sodium chloride solution. The yellowish coloured ethyl acetate phase is dried over sodium sulphate and evaporated under reduced pressure. For purification, the residue (120 mg) is chromatographed on silica gel with a 95:5 mixture of methylene chloride and methanol, which contains 0.1% ammonium hydroxide, as the eluting agent. After lyophilization from dioxan there are obtained 85 mg of (S)-α-[(S)-α-[(t-butylsulphonyl)methyl]hydrocinnamamido]-N-[(1S,2R,3S)-3-(1-cyclohexen-1-yl)-1-(cyclohexylmethyl)-2,3-dihydroxypropyl]Imidazole-4-propionamide as a yellowish powder, MS: 671 (M+H)+.

The (1S or R,2R,3S)-3-amino-4-cyclohexyl-1-(1-cyclohexen-1-yl)-1,2-butanediol used as the starting material was prepared as follows:

54.5 g (228 mmol) of (4S,5RS)-4-(cyclohexylmethyl)-5-vinyl-2-oxazolidinone (see J. Med. Chem., 30, 1729 (1987)] in 800 ml of methanol are cooled to −78° and ozone gas (3 g/hour) is conducted through the solution for 3.5 hours until a blue colour appears. Subsequently, ozone gas (1 g/hour) is conducted through the reaction mixture for a further 10 minutes, oxygen gas is conducted through for 5 minutes and argon is conducted through for 20 minutes, whereby the reaction mixture becomes colourless. Subsequently, 50 ml of dimethyl sulphide are added, the cooling bath is removed and the mixture is stirred at room temperature for 1 hour. Then, the reaction mixture is left to stand in a refrigerator overnight, thereafter stirred for a further 30 minutes and evaporated to dryness. The residue is extracted three times with 600 ml of ether each time and the organic phase is washed twice with 300 ml of water each time, dried over magnesium sulphate, filtered and evaporated, whereby there are obtained 54.5 g of a foam. This foam is dissolved in 150 ml of methanol and treated with 31.51 g (228 mmol) of potassium carbonate and stirred under argon at room temperature for 3 hours. Subsequently, the reaction mixture is poured into a mixture of ice and water (300 ml), extracted three times with 600 ml of ethyl acetate each time, the organic phase is washed with saturated sodium chloride solution, dried over magnesium sulphate, filtered and evaporated, whereby there are obtained 48.5 g of a foam. This crude product is chromatographed on 1.5 kg of silica gel with ethyl acetate as the eluting agent, whereby there are obtained 34.3 g (71%) of (4S,5R)-4-(cyclohexylmethyl)-2-oxo-5-oxazolidinecarboxaldehyde as a foam, MS: 211 (M)+, Rf value 0.15 in ethyl acetate.

65 ml (91.3 mmol) of a 1.4M solution of t-butyllithium in pentane are added at −78° with a syringe to a solution of 5.88 g (36.5 mmol) of 1-bromocyclohexene [see J. Org. Chem., 45, 5396 (1980) in 40 ml of tetrahydrofuran. After completion of the addition the mixture is stirred at 0° for 30 minutes and subsequently again cooled to −78°. To this cooled reaction solution are added 1.46 g (6.9 mmol) of (4S,5R)-4-(cyclohexylmethyl)-2-oxo-5-oxazolidinecarboxaldehyde dissolved in 20 ml of tetrahydrofuran. After completion of the addition the reaction mixture is allowed to warm slowly to room temperature and is stirred for a further 3 hours. For the working-up, the reaction mixture is concentrated under reduced pressure, diluted with ethyl acetate and washed in succession with ammonium chloride solution and saturated sodium chloride solution. The organic phase is dired over sodium sulphate and evaporated under reduced pressure, and the residue is chromatographed on silica gel with ether as the eluting agent. In this manner there are obtained 310 mg of the less polar (4S,5R)-4-(cyclohexylmethyl)-5-[(S or R)-1-(1-cyclohexen-1-yl)hydroxymethyl]-3-oxazolidinone as well as 250 mg of the more polar (4S,5R)-4-(cyclohexylmethyl)-5-[(R or S)-1-(1-cyclohexen-1-yl)hydroxymethyl]-2-oxazolidinone, MS for both epimers: 294 (M+H)+.

A mixture of 310 mg (1.05 mmol) of the aforementioned less polar epimer and 668 mg (2.1 mmol) of barium hydroxide [Ba(OH$_2$.8H$_2$O] in 20 ml of dioxan and 20 ml of water is heated to reflux for 12 hours. After cooling to room temperature carbon dioxide is conducted into the reaction mixture, the precipitate is subsequently filtered off and washed with hot dioxan. The combined dioxan solutions are evaporated under reduced pressure and the residue obtained is chromatographed on silica gel with a 95:5 mixture of methylene chloride and methanol which contains 0.1% ammonium hydroxide. In this manner there are obtained 115 mg of (1S. or R,2R,3S)-3-amino-4-cyclohexyl-1-(1-cyclohexen-1-yl)-1,2-butanediol as a colourless solid, MS: 263 (M+H)+.

The N-[(S)-α-[(t-butylsulphonyl)methyl]hydrocinnamoyl]-3-(2,4-dinitrophenyl)-L-histidine used as the starting material was prepared as follows:

15.8 g (65.5 mmol) of L-histidine methyl ester dihydrochloride, 18.6 g of (S)-α-[(t-butylsulphonyl)-methyl]-hydrocinnamic acid, 28.9 g of BOP and 35.8 ml of Hünig base are dissolved in 400 ml of acetonitrile and subsequently stirred at room temperature for 12 hours. After the usual working-up the crude produce is purified by flash chromatography on silica gel, whereby there are obtained 28 g (98%) of methyl (S)-α-[(S)-α-[(t-butylsulphonyl)methyl]hydrocinnamamido]imidazolepropionate as a resin, Rf value 0.25 in a 20:1 mixture of methylene chloride and methanol, MS: 435 (M)+.

23.3 g (54.6 mmol) of methyl (S)-α-[(S)-α-[(t-butylsulphonyl)methyl]hydrocinnamamido]imidazolepropionate in 250 ml of methylene chloride are treated with 7.43 ml (54.6 mmol) of triethylamine. Subsequently, 9.94 g (54.6 mmol) of 2,4-dinitro-1-fluorobenzene in 100 ml of methylene chloride are added dropwise within about 20 minutes while cooling with ice and the reaction mixture is stirred at room temperature until the reaction is complete, this being the case after 4 hours (checking by thin-layer chromatography). Usual working-up of the reaction mixture yields 20.5 g (62%) of N-[(S)-α-[(t-butylsulphonyl)methyl]hydrocinnamoyl]-1-(2,4-dinitrophenyl)-L-histidine methyl ester as a brown foam, Rf value 0.4 in a 30:1 mixture of methylene chloride and methanol, MS: 602 (M+H)+.

20.5 g (34.07 mmol) of N-[(S)-α-[(t-butylsulphonyl)-methyl]hydrocinnamoyl]-1-(2,4-dinitrophenyl)-L-histidine methyl ester are dissolved in 180 ml of dioxan, treated with 85 ml (170.34 mmol) of 2N hydrochloric acid and subsequently heated to 80° for 2.5 hours. Usual working-up and crystallization from ether/hexane yields 15.7 g (73%) of N-[(S)-α-[(t-butylsulphonyl)methyl]hydrocinnamoyl]-3-(2,4-dinitrophenyl)-L-histidine in the form of a pale yellow amorphous solid, Rf value 0.2 in a 5:1 mixture of methylene chloride and methanol, MS: 588 (M+H)+.

EXAMPLE 14

The following compounds were manufactured in an analogous manner to that described in Example 13:

From N-[(S)-α-[(t-butylsulphonyl)methyl]hydrocinnamoyl]-3-(2,4-dinitrophenyl)-L-histidine and (2S,3R,4R or S,Z)-2-amino-1-cyclohexyl-5-methyl-5-heptene-3,4-diol the (S)-α-[(S)-α-[(t-butylsulphonyl)methyl]hydrocinnamido]-N-[(1S,2R,3R or S,Z)-1-(cyclohexylmethyl)-2,3-dihydroxy-4-methyl-4-hexenyl]imidazole-4-phropionamide as a yellowish solid, MS: 671 (M+H)+;

from N-[(S)-α-[(t-butylsulphonyl)methyl]hydrocinnamoyl]-3-(2,4-dinitrophenyl)-L-histidine and (3S,4R,5S)-5-amino-6-cyclohexyl-2-methyl-1-hexene-3,4-diol the (S)-α-[(S)-α-(t-butylsulphonyl)methyl]hydrocinnamamido]-N-[(1S,2R,3S)-1-(cyclohexylmethyl)-2,3-dihydroxy-4-methyl-4-pentenyl]imidazole-4-propionamide as a colourless solid, MS: 631 (M+H)+;

from N-[(S)-α-[(t-butylsulphonyl)methyl]hydrocinnamoyl]-3-(2,4-dinitrophenyl)-L-histidine and (3R,4R,5S)-5-amino-6-cyclohexyl-2-methyl-1-hexene-3,4-diol the (S)-α-[(S)-α-[(t-butylsulphonyl)methyl]hydrocinnamamido]-N-[(1S,2R,3R)-1-(cyclohexylmethyl)-2,3-dihydroxy-4-methyl-4-pentenyl]imidazole-4-propionamide as a colourless solid, MS: 631 (M+H)+.

The amines used as the starting materials were prepared as follows:

(2S,3R,4R or S,Z)-2-Amino-1-cyclohexyl-5-methyl-5-heptene-3,4-diol

A solution of 7.2 g (34 mmol) of (4S,5R)-4-(cyclohexylmethyl)-2-oxo-5-oxazolidinecarboxaldehyde in 60 ml of tetrahydrofuran is added dropwise at 0° to a solution of the Grignard compound prepared from 18.6 g (137 mmol) of 2-bromo-2-butene (E/Z=2:3) and 3.34 g (137 mgram atom) of magnesium shavings in 90 ml of tetrahydrofuran. The reaction mixture is allowed to warm to room temperature and is stirred for a further 15 hours. For the working-up, the reaction mixture is hydrolyzed with 100 ml of ice-cold, saturated ammonium chloride solution and the organic phase is separated. The aqueous phase is extracted twice with 300 ml of ether each time. The combined organic phases are dried over sodium sulphate and evaporated under reduced pressure. For purification, the residue is chromatographed on silica gel with a 3:1 mixture of toluene and ethyl acetate as the eluting agent. In this manner there are obtained three fractions consisting of the two epimers and, respectively, the epimer mixture in the sequence of increasing polarity: 1.7 g of (4S,5R)-4-(cyclohexylmethyl)-5-[(S or R,Z)-1-hydroxy-2-methyl-2-butenyl]-2-oxazolidinone, MS: 206 (M-NH2-COOH)+, 0.7 g of (4S,5R)-4-(cyclohexylmethyl)-5-[(R or S,E or Z)-1-hydroxy-2-methyl-2-butenyl]-2-oxazolidinone, MS: 268 (M+H)+, and 1.5 g of (4S, 5R)-4-(cyclohexylmethyl)-5- -[(R or S,E or Z)-1-hydroxy-2-methyl-2-butenyl]-2-oxazolidinone, MS: 268 (M+H)+, in each case as a colourless solid.

A mixture of 800 mg (3 mmol) of (4S,5R)-4-(cyclohexylmethyl)-5-[(S or R,Z)-1-hydroxy-2-methyl-2-butenyl]-2-oxazolidinone and 1.89 g (6 mmol) of barium hydroxide [Ba(OH)2 . 8H2O] in 20 ml of dioxan and 20 ml of water is heated to reflux for 6 hours. After cooling to room temperature carbon dioxide is conducted into the reaction mixture and the precipitate formed is filtered off and washed with hot dioxan. The combined organic phases are evaporated under reduced pressure and the residue remaining is chromatographed on silica gel with a 95:5 mixture of methylene chloride and methanol, which contains 0.1% ammonium hydroxide, whereby there are obtained 461 mg of (2S,3R,4R or S,Z)-2-amino-1-cyclohexyl-5-methyl-5-heptene-3,4-diol as a colourless solid, MS:242 (M+H)+.

In an analogous manner to that described above, (4S,5R)-4-(cyclohexylmethyl)-2-oxo-5-oxazolidinecarboxaldehyde is converted in a Grignard reaction with propenyl-2-magnesium bromide into the two epimeric compounds (4S,5R)-4-(cyclohexylmethyl)-5-[(S)-1-hydroxy-2-methylallyl]-2-oxazolidinone and (4S,5R)-4-(cyclohexyl-methyl)-5-[(R)-1-hydroxy-2-methylallyl]-2-oxazolidinone which, after separation, are hydrolyzed to (3S,4R,5S)-5-amino-6-cyclohexyl-2-methyl-1-hexene-3,4-diol and, respectively, the epimeric compound (3R,4R,5S)-5-amino-6-cyclohexyl-2-methyl-1-hexene-3,4-diol.

EXAMPLE 15

In an analogous manner to that described in Example 13, by reacting (1RS,2R,3S)-3-amino-4-cyclohexyl-1-(2-furyl)-1,2-butanediol with N-[(S)-α-[(t-butylsulphonyl)methyl]hydrocinnamoyl]-3-(2,4-dinitrophenyl)-L-histidine there was obtained (S)-α-[(S)-α-[(t-butylsulphonyl)methyl]hydrocinnamamido]-N-[(1S,2R,3RS)-1-(cyclohexylmethyl)-2,3-dihydroxy-3-(2-furyl)propyl]imidazole-4-propionamide (1:1 mixture of epimers) as a pale yellow solid, MS: 657 (M+H)+. The more polar epimer (S)-α-[(S)-α-[(t-butylsulphonyl)methyl]hydrocinnamamido]-N-[(1S,2R,3R or S)-1-(cyclohexylmethyl)-2,3-dihydroxy-3-(2-furyl)propyl]imidazole-4-propionamide, MS: 657 (M+H)+, can be separated from the above mixture by chromatography.

The (1RS,2R,3S)-3-amino-4-cyclohexyl-1-(2-furyl)-1,2-butanediol used as the starting material was prepared as follows:

Reaction of (4S,5R)-4-(cyclohexylmethyl)-2-oxo-5-oxazolidinecarboxaldehyde with 2-lithiofuran (see Chemistry Letters 1982, page 1169) yields (4S,5R)-4-(cyclohexylmethyl)-5-[(RS)-α-hydroxy-2-furfuryl]-2-oxazolidinone (1:1 mixture of epimers) in the form of a resin, MS: 279 (M)+. Basic saponification of this compound in an analogous manner to that described in Example 14 yields (1RS,2R,3S)-3-amino-4-cyclohexyl-1-(2-furyl)-1,2-butanediol as a 1:1 mixture of epimers, MS: 254 (M+H)+.

EXAMPLE 16

750 mg (1.82 mmol) of t-butyl (4S,5R)-4-(cyclohexylmethyl)-5-[(R or S)-hydroxy-(2-thiazolyl)methyl]-2,2-dimethyl-3-oxazolidinecarboxylate are dissolved in 18 ml of methanol, 6.2 ml of 2N hydrochloric acid are added thereto and the mixture is subsequently heated to reflux for 2 hours. Thereafter, the solvent is removed under reduced pressure, the residue is taken up in a 10:1 mixture of ethyl acetate and methanol, the solution obtained is dried over sodium sulphate and evaporated under reduced pressure, whereby there are obtained 500 mg (80%) of the amine as the dihydrochloride in the form of a resin which are used in the next step without further purification.

250 mg (0.73 mmol) of the above product are dissolved in 40 ml of acetonitrile, 323 mg (0.73 mmol) or BOP, 354 mg (0.73 mmol) of 1-(t-butoxycarbonyl)-N-[(R)-α-(3,3-dimethyl-2-oxobutyl)hydrocinnamoyl]-L-histidine and 0.4 ml (2.33 mmol) of Hünig base are added thereto and the reaction solution is stirred at room temperature for 14 hours. After the usual working-up there are obtained 324 mg (60%) of a brown-yellow resin which is dissolved in 10 ml of methanol, treated with 20 mg of potassium carbonate and stirred at room temperature for 2 hours. After the usual working-up there is obtained a crude product which, for purification, is chromatographed on silica gel using a 10:1 mixture of methylene chloride and methanol as the eluting agent. In this manner there are obtained 96.2 mg (34%) of (S)-N-[(1S,2R,3S or R)-1-(cyclohexylmethyl)-2,3-dihydroxy-3-(2-thiazolyl)propyl]-α-[(R)-α-(3,3-dimethyl-2-oxobutyl)hydrocinnamamido]imidazole-4-propionamide as a resin, MS: 638 (M+H)+.

The following compounds were manufactured in an analogous manner to that described above:

From 1-(t-butoxycarbonyl)-N-[(R)-α-(3,3-dimethyl-2-oxobutyl)hydrocinnamoyl]-L-histidine and t-butyl (4S,5R)-4-(cyclohexylmethyl)-5-[(S or R)-hydroxy-(2-thiazolyl)methyl]-2,2-dimethyl-3-oxazolidinecarboxylate the (S)-N-[(1S,2R,3R or S)-1-(cyclohexylmethyl)-2,3-dihydroxy-3-(2-thiazolyl)propyl]-α-[(R)-α-3,3-dimethyl-2-oxobutyl)hydrocinnamamido]imidazole-4-propionamide as a resin, MS: 638 (M+H)+;

from 1-(t-butoxycarbonyl)-N-[(R)-α-(3,3-dimethyl-2-oxobutyl)hydrocinnamoyl]-L-histidine and t-butyl (4S,5R)-4-(cyclohexylmethyl)-2,2-dimethyl-5-[(αR or S,2R or S)-tetrahydro-2-hydroxy-2-furfuryl]-3-oxazolidinecarboxylate or t-butyl (4S,5R)-4-(cyclohexylmethyl)-2,2-dimethyl-5-[(αR or S,2S or R)-tetrahydro-2-hydroxy-2-furfuryl]-3-oxazolidinecarboxylate the (S)-N-[(1S,2R,3R or S)-1-(cyclohexylmethyl)-2,3-dihydroxy-3-[(R or S)-tetrahydro-2-furyl]propyl]-α-[(R)-α-(3,3-dimethyl-2-oxobutyl)hydrocinnamamido]imidazole-4-propionamide as well as the epimeric (S)-N-](1S,2R,3R or S)-1-(cyclohexylmethyl)-2,3-dihydroxy-3-[(S or R)-tetrahydro-2-furyl]-propyl]-α-[(R)-α-(3,3-dimethyl-2-oxobutyl)hydrocinnamamido]imidazole-4-propionamide, both as a colourless amorphous solid, MS (in each case): 625 (M+H)+.

The 1-(t-butoxycarbonyl)-N-[(R)-α-(3,3-dimethyl-2-oxobutyl)hydrocinnamoyl]-L-histidine used as the starting material was prepared as follows:

A suspension of 3.0 g (12 mmol) of (R)-α-(pivaloylmethyl)hydrocinnamic acid (see EPA 0.184.550) and 2.66 g (11 mmol) of L-histidine methyl ester dihydrochloride in 340 ml of dimethylformamide is treated at room temperature under a nitrogen atmosphere with 3.45 g (34 mmol) of triethylamine and 4.58 g (12 mmol) of HBTU. The reaction mixture is stirred at room temperature for 5 hours and subsequently evaporated in a high vacuum. The residue is dissolved in 500 ml of ethyl acetate and washed in succession with 100 ml of water, three times with 100 ml of saturated sodium bicarbonate solution each time and 100 ml of saturated sodioum chloride solution. The organic phase is dried over sodium sulphate, evaporated under reduced pressure and the yellowish crude product obtained is chromatographed on silica gel with a 95:5 mixture of methylene chloride and methanol which contains 0.1% ammonia. In this manner there are obtained 3.6 g of N-[(R)-α-(3,3-dimethyl-2-oxobutyl)hydrocinnamoyl]-L-histidine methyl ester as a colourless foam, MS: 399 (M)+.

A solution of 3.56 g (8.9 mmol) of N-[(R)-α-(3,3-dimethyl-2-oxobutyl)hydrocinnamoyl]-L-histidine methyl ester and 9.36 ml of 1N sodium hydroxide solution in 50 ml of methanol is stirred at room temperature for 15 hours and then evaporated under reduced pressure in the cold. The residue is dissolved in 70 ml of dioxan and 30 ml of water, a solution of 2.95 (13.5 mmol) of di-t-butyl dicarbonate is added dropwise at room temperature and the mixture is thereafter stirred at room temperature for 15 hours. For the working-up, the reaction solution is concentrated under reduced pressure to about ⅓ of its volume and then diluted with 200 ml of ethyl acetate. After adding 50 ml of ice-water the reaction mixture is adjusted to pH 2.5 and the aqueous phase is saturated with solid sodium chloride. The aqueous phase is extracted two times with ethyl acetate and the combined ethyl acetate phases are dried over sodium sulphate and evaporated. The crude product obtained is chromatographed on silica gel with a 95:5 mixture of methylene chloride and methanol which contains 0.1% acetic acid, whereby there are obtained 3.5 g of 1-(t-butoxycarbonyl)-N-[(R)-α-(3,3-dimethyl-2-oxobutyl)hydrocinnamoyl]-L-histidine as a colourless powder, MS: 486 (M+H)+.

The t-butyl (4S,5R)-4-(cyclohexylmethyl)-5-[(R or S)-hydroxy-(2-thiazolyl)methyl]-2,2-dimethyl-3-oxazolidinecarboxylate and t-butyl (4S,5R)-4-(cyclohexylmethyl)-5-[(S or R)-hydroxy-(2-thiazolyl)methyl]-2,2-dimethyl-3-oxazolidinecarboxylate used as the starting materials were prepared as follows:

14.7 g (51.86 mmol) of t-butyl (1S,2S:2R=2:1)-1-(cyclohexylmethyl)-2-hydroxy-3-butenyl carbamate [J. Med. Chem., 30, 1729 (1987)] in 150 ml of 2,2-dimethoxypropane are treated with 832 mg (4.37 mmol) of p-toluenesulphonic acid monohydrate and the reaction solution is stirred at room temperature for 3 hours. Thereafter, the reaction solution is diluted with 600 ml of ethyl acetate and washed with 2N potassium bicarbonate solution. The organic phase is worked-up in the usual manner and the crude product obtained is purified by chromatography on silica gel with an 80:1 mixture of methylene chloride and ethyl acetate, whereby there are obtained 11.5 g (68%) of t-butyl (4S,5S:5R=2:1)-4-(cyclohexylmethyl)-2,2-dimethyl-5-vinyl-3-oxazolidinecarboxylate, MS: 308 (M-CH3)+; Rf value 0.5 in an 80:1 mixture of methylene chloride and ethyl acetate.

11.5 g (35.55 mmol) of t-butyl (4S,5S:5R=2:1)-4-(cyclohexylmethyl)-2,2-dimethyl-5-vinyl-3-oxazolidinecarboxylate are dissolved in 200 ml of methanol, the solution is cooled to −78° and ozone gas is conducted through the solution until a blue colouration occurs (about 40 minutes). Thereafter, the ozone supply is shut off and argon is conducted through the solution at −75° until the blue colouration disappears (about 15 minutes). Subsequently, 5.0 ml (35.55 mmol) of dimethyl sulphide are added at −75°, the reaction mixture is allowed to warm to room temperature and argon is conducted through the solution for a further 2 hours before it is evaporated under reduced pressure. The residue obtained (16 g of a pale yellow liquid) is dissolved in 260 ml of methanol, treated with 3.05 g of potassium carbonate and stirred at room temperature for 2 hours. Subsequently, the mixture is partitioned between ethyl acetate and water, the organic phase is worked-up in the usual manner and the crude product is chromatographed on silica gel with a 20:1 mixture of methylene chloride and ethyl acetate as the eluting agent, whereby there are obtained 7.2 g (62%) of t-butyl (4S,5R)-4-(cyclohexylmethyl)-5-formyl-2,2-dimethyl-3-oxazolidinecarboxylate as a yellow resin, MS: 310 (M-CH3)+; Rf value 0.4 in a 20:1 mixture of methylene chloride and ethyl acetate.

4.67 ml of thiazole (65.7 mmol) in 150 ml of tetrahydrofuran are cooled to −78° and at this temperature there are added dropwise 41.3 ml of a 1.6M solution of butyllithium in hexane (66.1 mmol). Thereafter, the rose coloured solution is stirred at −78° for a further 15 minutes and then treated dropwise with 5.37 g (16.5 mmol) of t-butyl (4S,5R)-4-(cyclohexylmethyl)-5-formyl-2,2-dimethyl-3-oxazolidinecarboxylate. Thereafter, the cooling bath is removed and the reaction mixture is allowed to warm to room temperature, it is decomposed with water and extracted with ethyl acetate. After the usual further working-up the two epimers formed are purified and isolated by chromatography on silica gel using a 4:1 mixture of hexane and ethyl acetate, whereby there are obtained 600 mg (9%) of t-butyl (4S,5R)-4-(cyclohexylmethyl)-5-[(R or S)-hydroxy-(2-thiazolyl)methyl]-2,2-dimethyl-3-oxazolidinecarboxylate (Rf value 0.4 in a 4:1 mixture of ether and hexane) and 1.4 g (20%) of t-butyl (4S,5R)-4-(cyclohexylmethyl)-5-[(S or R)-hydroxy-(2-thiazolyl)methyl]-2,2-dimethyl-3-oxazolidinecarboxylate (Rf value 0.35 in a 4:1 mixture of ether and hexane), in each case as a brown solid, MS (in each case): 411 (M)+.

The t-butyl (4S,5R)-4-(cyclohexylmethyl)-2,2-dimethyl-5-[(αR or S,2R or S)-tetrahydro-2-hydroxy-2-furfuryl]-3-oxazolidinecarboxylate and t-butyl (4S,5R)-4-(cyclohexylmethyl)-2,2-dimethyl-5-[(αR or S,2S or R)-tetrahydro-2-hydroxy-2-furfuryl]-3-oxazolidinecarboxylate used as the starting materials were prepared as follows:

In an analogous manner to that described in Example 15, t-butyl (4S,5R)-4-(cyclohexylmethyl)-5-formyl-2,2-dimethyl-3-oxazolidinecarboxylate was reacted with 2-lithiofuran, whereby there was obtained a 1:2 mixture epimers of t-butyl (4S,5R)-4-(cyclohexylmethyl)-5-[(S or R)-α-hydroxyfurfuryl]-2,2-dimethyl-3-oxazolidinecarboxylate (Rf value 0.5 in a 20:1 mixture of methylene chloride and methanol) and t-butyl (4S,5R)-4-(cyclohexylmethyl)-5-[(R or S)-α-hydroxyfurfuryl]-2,2-dimethyl-3-oxazolidinecarboxylate (Rf value 0.45 in a 20:1 mixture of methylene chloride and methanol) as yellow coloured crystals which can be separated readily by chromatography MS (in each case): 322 (M-CH₃-isobutene)+.

500 mg of t-butyl (4S,5R)-4-(cyclohexylmethyl)-5-[(S or R)-α-hydroxyfurfuryl]-2,2-dimethyl-3-oxazolidinecarboxylate are dissolved in 150 ml of ethanol, 0.5 g of rhodium/aluminum oxide is added and the mixture is hydrogenated for 48 hours in an autoclave at a pressure of 10 bar and at 50°. Thereafter, the catalyst is filtered off, the solvent is evaporated under reduced pressure and the crude product, consistinf of the two epimeric compounds, is chromatographed for separation and purification, whereby there are obtained 170 mg (34%) of t-butyl (4S,5R)-4-(cyclohexylmethyl)-2,2-dimethyl-5-[(αR or S,2R or S)-tetrahydro-2-hydroxy-2-furfuryl]-3-oxazolidinecarboxylate (Rf value 0.5 in a 1:1 mixture of petroleum ether and ether) and 176 mg (35%) of t-butyl (4S,5R)-4-(cyclohexylmethyl)-2,2-dimethyl-5-[(αR or S,2S or R)-tetrahydro-2-hydroxy-2-furfuryl]-3-oxazolidinecarboxylate (Rf value 0.4 in a 1:1 mixture of petroleum and ether), MS (in each case): 398 (M+H)+.

EXAMPLE 17

In an analogous manner to that described in Example 16, by reacting t-butyl (4S,5R)-4-(cyclohexylmethyl)-5-[(R or S)-hydroxy-[(R or S)-tetrahydro-2-furyl]methyl]-2,2-dimethyl-3-oxazolidinecarboxylate with N-[(S)-α-[(t-butylsulphonyl)methyl]hydrocinnamoyl]-3-(2,4-dinitrophenyl)-L-histidine there is obtained (S)-α-[(S)-α-[(t-butylsulphonyl)methyl]hydrocinnamamido]-N-[(1S,2R,3R or S)-1-(cyclohexylmethyl)-2,3-dihydroxy-3-[(R or S)-tetrahydro-2-furyl]propyl]imidazole-4-propionamide in the form of a yellow amorphous powder, MS: 827 (M+H)+. The cleavage of the dinitropheyl group with thiolactic acid is effected in an analogous manner to Example 13 and yields (S)-α-[(S)-α-[(t-butylsulphonyl)methyl]hudrocinnamamido]-N-[(1S,2R,3R or S)-1-(cyclohexylmethyl)-2,3-dihydroxy-3-[(R or S)-tetrahydro-2-furyl]propyl]imidazole-4-propionamide as a pale yellow amorphous solid, MS: 661 (M+H)+.

The protected propionamide used as the starting material was prepared as follows:

In an analogous manner to that described in Example 16, from t-butyl (4S,5R)-4-(cyclohexylmethyl)-5-[(R or S)-α-hydroxyfurfuryl]-2,2-dimethyl-3-oxazolidinecarboxylate there were prepared t-butyl (4S,5R)-4-(cyclohexylmethyl)-5-[(R or S)-hydroxy-[(R or S)-tetrahydro-2-furyl]methyl]-2,2-dimethyl-3-oxazolidinecarboxylate and t-butyl (4S,5R)-4-(cyclohexylmethyl)-5-[(R or S)-hydroxy-[(S or R)-tetrahydro-2-furyl]methyl]-2,2-dimethyl-3-oxazolidinecarboxylate, whereby the two epimers were isolated from the 1:1 mixture of epimers obtained, Rf value 0.5 and, respectively, 0.4 in a 1:1 mixture of ether and hexane, MS (in each case): 398 (M+H)+.

EXAMPLE 18

The following compounds were manufactured in an analogous manner to that described in Examples 1 and 4:

(S)-N-[(1S,2RS,3RS,4SR)-5-(Benzyloxy)-1-(cyclohexylmethyl)-2,3-dihydroxy-4-methylpentyl]-α-[(S)-α-[(t-butylsulphonyl)methyl]hydrocinnamamido]imidazole-4-propionamide as a solid, melting point 89° (from methylene chloride/ether/hexane) and the epimeric (S)-N-[(1S,2S or R,3S or R,4SR)-5-(benzyloxy)-1-(cyclohexylmethyl)-2,3-dihydroxy-4-methylpentyl]-α-[(S)-α-[(t-butylsulphonyl)methyl]hydrocinnamamido]imidazole-4-propionamide as a solid, melting point 95° (from methylene chloride/ether/hexane), whereby, however, rac. 3-benzyloxy-2-methyl-1-propyl bromide was used for the preparation of the Grignard reagent;

(S)-α-[(S)-α-[(t-butylsulphonyl)methyl]hydrocinnamamido]-N-[(1S,2R,3S)-1-(cyclohexylmethyl)-3-cyclopentyl-2,3-dihydroxypropyl]imidazole-4-propionamide as a solid, melting point >125° (dec.), whereby cyclopentyl bromide was used for the preparation of the Grignard reagent;

(R)-α-[(S)-α-[(t-butylsulphonyl)methyl]hydrocinnamamido]-N-[(1S,2R,3S)-1-(cyclohexylmethyl)-3-cyclopropyl-2,3-dihydroxypropyl]-4-thiazolepropionamide as a white solid, melting point 75° (dec.; from methylene chloride/ether/hexane) and the epimeric (S)-α-[(S)-α-[(t-butylsulphonyl)methyl]hydrocinnamamido]-N-[(1S,2R,3S)-1-(cyclohexylmethyl)-3-cyclopropyl-2,3-dihydroxypropyl]-4-thiazolepropionamide as a white solid, melting point 91° (dec.; from methylene chloride/ether/hexane), whereby cyclopropyl bromide was used for the preparation of the Grignard reagent and in place of (Fmoc)₂His-OH there was used Boc-(RS)-thiazolylalanine which, in turn, was prepared according to S. Rosenberg et al., S. Med. Chem., 30, 1224 (1987);

(S)-α-[(t-butylsulphonyl)methyl]-N-[(S)-2-t-butoxy-1-[[(1S,2R,3S)-1-(cyclohexylmethyl)-2,3-dihydroxy-4-methylpentyl]carbamoyl]ethyl]hydrocinnamamide as a white solid, melting point 167° (from ethylene chloride/ether/hexane), whereby isopropyl bromide was used for the preparation of the Grignard reagent and (Fmoc)Ser(O-t-butyl) was used in place of (Fmoc)₂His-OH;

(S)-α-[(S)-α-[(t-butylsulphonyl)methyl]hydrocinnamamido]-N-[(1S,2R,3S)-1-(cyclohexylmethyl)-2,3-dihydroxy-4-methyl]pentyl]-2-thiophenepropionamide as a white solid, melting point 176° (from methylene chloride/ether), whereby isopropyl bromide was used for the preparation of the Grignard reagent and Boc-thienylalanine was used in place of (Fmoc)₂His-OH.

EXAMPLE 19

A methanolic solution of (S)-N-[(1S,2R or S,3R or S,4R)-5-(benzyloxy)-1-(cyclohexylmethyl)-2,3-dihydroxy-4-methylpentyl]-α-[(S)-α-[(t-butylsulphonyl)methyl]-hydrocinnamido]imidazole-4-propionamide is stirred in a hydrogen atmosphere overnight with 5% palladium-on-charcoal. Thereafter, the catalyst is filtered off and the filtrate is concentrated, whereby there is obtained (S)-α-[(S)-α-[(t-butylsulphonyl)methyl]hydrocinnamamido]-N-[(1S,2S or R,3S or R,4SR)-1-(cyclohexylmethyl)-2,3,5-trihydroxypentyl]imidazole-4-propionamide as a foam, MS: 649 (M+H)⁺.

In an analogous manner, from (S)-N-[(1S,2S or R,3S or R,4SR)-5-(benzyloxy)-1-(cyclohexylmethyl)-2,3-dihydroxy-4-methylpentyl]-α-[(S)-α-[(t-butylsulphonyl)methyl]-hydrocinnamido]imidazole-4-propionamide there is obtained (S)-α-[(S)-α-[(t-butylsulphonyl)methyl]hydrocinnamamido]-N-[(1S,2RS,3RS,4SR)-1-(cyclohexylmethyl)-2,3,5-trihydroxypentyl]imidazole-4-propionamide in the form of a foam, MS 649 (M+H)⁺.

EXAMPLE 20

In an analogous manner to that described in Example 10, from (S)-α-[(S)-α-[(t-butylsulphonyl)-methyl]hydrocinnamamido]-N-[(1S,2R,3S)-1-(cyclohexylmethyl)-3-cyclopropyl-2,3-dihydroxypropyl]imidazole-4-propionamide and chloroacetic anhydride/triethylamine in place of acetic anhydride/formic acid/pyridine there was obtained (1S,2R)-2-[(S)-1-[(S)-α-[(S)-α-[(t-butylsulphonyl)methyl]hydrocinnamamido]imidazole-4-propionamido]-2-cyclohexylethyl]-1-cyclopropylethylene bis(chloroacetate) as a solid, MS: 793 (M+H)⁺. This compound was converted by heating to reflux in diethylamine for 90 minutes into (1S,2R)-2-[(S)-1-[(S)-α-[(S)-α-[(t-butylsulphonyl)methyl]hydrocinnamamido]-imidazole-4-propionamido]-2-cyclohexylethyl]-1-cyclopropyethylene bis(diethylaminoacetate), MS 857 (M+H)⁺.

EXAMPLE A

A sterile filtered aqueous solution of (S)-α-[(S)-α-[(t-butylsulphonyl)methyl]hydrocinnamamido]-N-[(1S,2R,3S)-1-(cyclohexylmethyl)-2,3-dihydroxy-4-methylpentyl]imidazole-4-propionamide is mixed while warming with a sterile gelatine solution, which contains phenol as a preserving agent, under aseptic conditions so that 1.0 ml of solution has the following composition:

| | |
|---|---|
| (S)-α-[(S)-α-[(t-Butylsulphonyl)-methyl]hydrocinnamamido]-N-[(1S,2R,3S)-1-(cyclohexylmethyl)-2,3-dihydroxy-4-methylpentyl]imidazole-4-propionamide | 3.0 mg |
| Gelatine | 150.0 mg |
| Phenol | 4.7 mg |
| Dist. water ad | 1.0 ml |

The mixture is filled into vials of 1.0 ml under aseptic conditions.

EXAMPLE B 5 mg of (S)-α-[(S)-α-[(t-butylsulphonyl)methyl]-hydrocinnamamido]-N-[(1S, 2R,3S)-1-(cyclohexylmethyl)-2,3-dihydroxy-4-methylpentyl]imidazole-4-propionamide are dissolved in 1 ml of an aqueous solution with 20 mg of mannitol. The solution is filtered sterile and filled under aseptic conditions into a 2 ml ampoule, cooled to a low temperature and lyophilized. Prior to administration the lyophilizate is dissolved in 1 ml of distilled water or 1 ml of physiological saline. The solution is used intramuscularly or intravenously. This formulation can also be filled into double chamber injection ampoules.

EXAMPLE C 500 mg of finely milled (5.0 μm) (S)-α-[(S)-α-[(t-butylsulphonyl)methyl]hydrocinnamamido]-N--[(1S,2R,3S)-1-(cyclohexylmethyl)-2,3-dihydroxy-4-methylpentyl]imidazole-4-propionamide are suspended in a mixture of 3.5 ml of Myglyol 812 (caprylic/capric triglyceride) and 0.08 g of benzyl alcohol. This suspension is filled into a container having a dosage valve. 5.0 g of Freon 12 (dichlorodifluoromethane) are filled into the container through the valve under pressure. The Freon is dissolved in the Myglyol-benzyl alcohol mixture by shaking. This spray container contains about 100 individual dosages which can be applied individually.

EXAMPLE D

When following the procedures described in Examples A-C, corresponding galenical preparations can be produced from the following, likewise preferred compounds:

(S)-N-[(1S,2R,3S)-1-(Cyclohexylmethyl)-3-cyclopropyl-2,3-dihydroxypropyl]-α-[(R)-α-(3,3-dimethyl-2-oxobutyl)hydrocinnamamido]imidazole-4-propionamide;

(S)-α-[(S)-α-[(t-butylsulphonyl)methyl]hydrocinnamamido]-N-[(1S,2R,3S)-1-(cyclohexylmethyl)-3-cyclopropyl-2,3-dihydroxypropyl]imidazole-4-propionamide;

(S)-α-[(S)-α-[(t-butylsulphonyl)methyl]hydrocinnamamido]-N-[(1S,2R,3S)-3-cyclobutyl-1-(cyclohexylmethyl)-2,3-dihydroxypropyl]imidazole-4-propionamide;

(S)-N-[(S)-1-[(2R or S,4R,5S)-2-t-butyl-5-isopropyl-1,3-dioxolan-4-yl]-2-cyclohexylethyl]-α-[(S)-α-[(t-butylsulphonyl)methyl]hydrocinnamamido]imidazole-4-propionamide;

(1S,2R)-[(S)-1-[(S)-α-[(S)-α-[(t-butylsulphonyl)-methyl]hydrocinnamamido]imidazole-4-propionamido]-2-cyclohexylethyl]-1-isopropylethylene bis(methoxyacetate);

(S)-α-[(S)-α-[(t-butylsulphonyl)methyl]hydrocinnamamido]-N-[(1S,2R,3S)-1-(cyclohexylmethyl)-3-cyclopentyl-2,3-dihydroxypropyl]imidazole-4-propionamide;

(S)-α-[(S)-α-[(t-butylsulphonyl)methyl]hydrocinnamamido]-N-[(1S,2R,3S)-1-(cyclohexylmethyl)-3-cyclopropyl-2,3-dihydroxypropyl]-4-thiazolepropionamide and (S)-α-[(S)-α-[(t-butylsulphonyl)methyl]hydrocinnamamido]-N-[(1S,2S or R,3S or R,4SR)-1-(cyclohexylmethyl)-2,3,5-trihydroxypentyl]imidazole-4-propionamide.

We claim:

1. A method for treating high blood pressure and cardiac insufficiency which comprises administering an effective amount of a compound of formula:

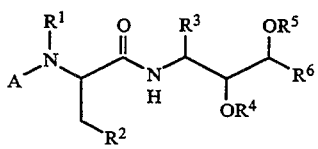     I wherein $R^1$ is hydrogen or methyl, $R^2$ is imidazol-4-yl, $R^3$ is isobutyl, cyclohexylmethyl or benzyl, $R^4$ and $R^5$ each independently are hydrogen, alkanoyl, which is optionally mono- or multiply-substituted by amino, monoalkylamino, dialkylamino, alkanoylamino, alkanoyloxyamino, carboxy, alkoxy or hydroxy, or an O-protecting group or together are a cyclic O-protecting group, $R^6$ is one of the groups:

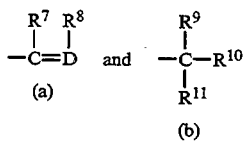

and A is the group:

—Y—Z wherein D is a methyne group or a nitrogen atom, $R^7$ is alkyl, aryl or arylalkyl and $R^8$ is hydrogen, alkyl, aryl or arylalkyl or $R^7$ and $R^8$ together with the two atoms to which they are attached is aryl, heteroaryl, cycloalkenyl or heterocycloalkenyl, $R^9$ is hydrogen or alkyl and $R^{10}$ and $R^{11}$ taken together with the carbon atom to which they are attached, are cycloalkyl or heterocycloalkyl, Y is the bivalent residue of optionally N- and α-methylated phenylalanine, cyclohexyalanine, tyrosine, O-methyltyrosine, α-napththylalanine or homophenylalanine linked with Z at the N-terminal, Z is acyl, in the form of an optically pure diastereomer, a diastereomeric racemate, or mixtures thereof as well as pharmaceutically usable salts thereof.

2. The method of claim 1, wherein $R^2$ signifies imidazol-4-yl, $R^4$ and $R^5$ each independently signify hydrogen, alkanoyl, which is optionally mono- or multiply-substituted by carboxy, alkoxy or hydroxy, or an O-protecting group or together signify a cyclic O-protecting group.

3. The method of claim 2, wherein $R^2$ signifies imidazol-4-yl, $R^4$ and $R^5$ each signify hydrogen, $R^7$ and $R^8$ each independently signify alkyl, aryl or arylalkyl or, together with the two atoms to which they are attached, aryl, heteroaryl, cycloalkenyl or heterocycloalkenyl.

4. The method of claim 1, wherein $R^1$ signifies hydrogen, $R^2$ signifies imidazol-4-yl, $R^3$ signifies cyclohexylethyl, $R^4$ and $R^5$ each independently signify hydrogen or alkanoyl, which is optionally mono-substituted by dialkylamino, carboxy or alkoxy, or together signify a cyclic O-protecting group, D signifies a methyne group, $R^7$ signifies alkyl and $R^8$ signifies hydrogen or alkyl or $R^7$ and $R^8$ together with the two atoms to which they are attached signify aryl, heteroaryl or cycloalkenyl, Y signifies the bivalent residue of phenylalanine linked with Z at the N-terminal and Z signifies acyl.

5. The method of claim 4, wherein $R^2$ signifies imidazol-4-yl, $R^4$ and $R^5$ each independently signify hydrogen or alkanoyl, which is optionally mono-substituted by methoxy, or together signify the acetal of pivalic aldehyde, $R^6$ signifies the group (b), $R^9$ signifies hydrogen, and $R^{10}$ and $R^{11}$ taken together with the carbon atom to which they are attached, signify cycloalkyl.

6. The method of claim 2, wherein $R^2$ signifies imidazol-4-yl, $R^4$ and $R^5$ each signify hydrogen and $R^{10}$ and $R^{11}$ taken together with the carbon atom to which they are attached, signify cyclopropyl or cyclobutyl.

7. A method for treating high blood pressure and cardiac insufficiency which comprises administering an effective amount of a compound of the formula

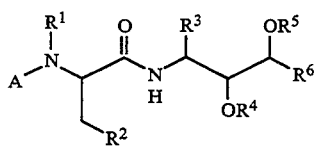     I wherein $R^1$ signifies hydrogen or methyl, $R^2$ signifies imidazol-4-yl, $R^3$ signifies isobutyl, cyclohexylmethyl or benzyl, $R^4$ and $R^5$ each independently signify hydrogen, alkanoyl, which is optionally mono- or multiply-substituted by amino, monoalkylamino, dialkylamino, alkanoylamino, alkanoyloxyamino, carboxy, alkoxy or hydroxy, or an O-protecting group or together signify a cyclic O-protecting group, $R^6$ signifies one of the groups

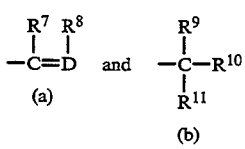

and A signifies the group

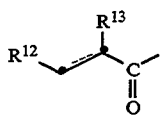

wherein D signifies a methyne group or a nitrogen atom, $R^7$ signifies alkyl, aryl or arylalkyl and $R^8$ signifies hydrogen, alkyl, aryl or arylalkyl or $R^7$ and $R^8$ together with the two atoms to which they are attached signify aryl, heteroaryl, cycloalkenyl or heterocycloalkenyl, $R^9$ signifies hydrogen or alkyl and $R^{10}$ and $R^{11}$ each independently signify alkyl, aryl, arylalkyl, cycloalkyl or the group

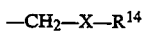

—CH$_2$—X—R$^{14}$     (e)

or, together with the carbon atom to which they are attached, cycloalkyl or heterocycloalkyl, with the proviso that, where $R^9$ signifies alkyl, $R^{10}$ and $R^{11}$ also signify alkyl, the dotted line can signify an additional bond, $R^{12}$ signifies phenyl, substituted phenyl, benzyl or naphthyl and $R^{13}$ signifies alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, alkylthioalkyl, alkylsulphinylalkyl or alkylsulphonylalkyl, X signifies an oxygen or sulphur atom or the group —NH— and $R^{14}$ signifies hydrogen, alkyl, cycloalkyl, arylalkyl, cycloalkylalkyl, alkylcarbonyl, arylcarbonyl or arylalkylcarbonyl, in the form of an optically pure diastere9mer, a diastereomeric racemate, or mixtures thereof as well as pharmaceutically usable salts thereof, and a therapeutically inert excipient.

8. The method of claim 7, wherein $R^2$ signifies imidazol-4-yl, $R^4$ and $R^5$ each independently signify hydrogen, alkanoyl, which is optionally mono- or multiply-substituted by carboxy, alkoxy or hydroxy, or an O-protecting group or together signify a cyclic O-protecting group and $R^{12}$ signifies phenyl, substituted phenyl or naphthyl.

9. The method of claim 7, wherein $R^2$ signifies imidazol-4-yl, $R^4$ and $R^5$ each signify hydrogen, $R^7$ and $R^8$ each independently signify alkyl, aryl or arylalkyl or, together with the two atoms to which they are attached, aryl, heteroaryl, cycloalkenyl or heterocycloalkenyl and $R^{14}$ signifies alkyl, cycloalkyl, arylalkyl, cycloalkylalkyl, alkyl-carbonyl, arylcarbonyl or arylalkylcarbonyl.

10. The method of claim 7, wherein $R^1$ signifies hydrogen, $R^2$ signifies imidazol-4-yl, $R^3$ signifies cyclohexylmethyl, $R^4$ and $R^5$ each independently signify hydrogen or alkanoyl, which is optionally mono-substituted by dialkylamino, carboxy or alkoxy, or together monosubstituted by dialkylamino, carboxy or alkoxy, or together signify a cyclic O-protecting group, D signifies a methyne group, $R^7$ signifies alkyl and $R^8$ signifies hydrogen or alkyl or $R^7$ and $R^8$ together with the group (e) or, together with the carbon atoms to which they are attached, cycloalkyl or heterocycloalkyl, $R^{13}$ signifies alkylcarbonylalkyl, heterocycloalkylcarbonylalkyl, alkyl-sulphinylalkyl or alkylsulphonylalkyl, X signifies an oxygen atom and $R^{14}$ signifies hydrogen or arylalkyl.

11. The method of claim 10, wherein $R^{13}$ signifies alkylcarbonylalkyl, heteroycloalkylcarbonylalkyl or alkylsulphonylalkyl.

12. The method of claim 11, wherein $R^2$ signifies imidazol-4-yl $R^4$ and $R^5$ each independently signify hydrogen or alkanoyl, which is optionally mono-substituted by methoxy, or together signify the acetal of pivalic aldehyde, $R^6$ signifies the group (b), $R^9$ signifies hydrogen, $R^{10}$ and $R^{11}$ each independently signify alkyl or, together with the carbon atom to which they are attached, cycloalkyl, $R^{12}$ signifies phenyl or substituted phenyl, and $R^{13}$ signifies alkylcarbonylalkyl or alkylsulphonylalkyl.

13. The method of claim 12, wherein $R^2$ signifies imidazol-4-yl, $R^4$ and $R^5$ each signify hydrogen, $R^{10}$ and $R^{11}$ taken together with the carbon atom to which they are attached signify cyclopropyl or cyclobutyl, $R^{12}$ signifies phenyl and $R^{13}$ signifies $C_1$-$C_4$-alkylcarbonylmethyl or $C_1$-$C_4$-alkylsulphonylmethyl.

14. A compound of the formula:

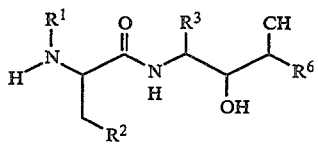

II wherein $R^1$ signifies hydrogen or methyl, $R^2$ signifies imidazol-4-yl, $R^3$ signifies isobutyl, cyclohexylmethyl or benzyl and $R^6$ signifies one of the groups:

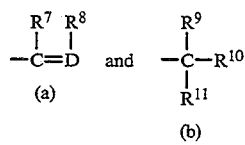

wherein D signifies a methyne group or a nitrogen atom, $R^7$ signifies alkyl, aryl or arylalkyl and $R^8$ signifies hydrogen, alkyl, aryl or arylalkyl or $R^7$ and $R^8$ together with the two atoms to which they are attached signify aryl, heteroaryl, cycloalkenyl or heterocycloalkenyl, $R^9$ signifies hydrogen or alkyl and $R^{10}$ and $R^{11}$ each independently signify alkyl, aryl, arylalkyl, cycloalkyl or the group

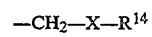

or together with the carbon atom to which they are attached, cycloalkyl or heterocycloalkyl, X is an oxygen or sulfur atom or the group —NH— and $R^{14}$ signifies hydrogen, alkyl, cycloalkyl, arylalkyl, cycloalkylalkyl, alkylcarbonyl, arylcarbonyl or arylalkylcarbonyl with the proviso that, where $R^9$ signifies alkyl, $R^{10}$ and $R^{11}$ also signify alkyl.

15. A pharmaceutical composition comprising an amount effective for the control of high blood pressure and cardiac insufficiency of a compound of formula:

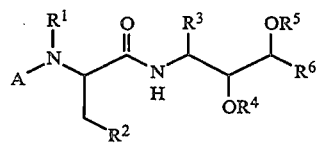

I wherein $R^1$ is hydrogen or methyl, $R^2$ is imidazol-4-yl, $R^3$ is isobutyl, cyclohexylmethyl or benzyl, $R^4$ and $R^5$ each independently are hydrogen, alkanoyl, which is optionally mono- or multiply-substituted by amino, monoalkylamino, dialkylamino, alkanoylamino, alkanoyloxyamino, carboxy, alkoxy or hydroxy, or an O-protecting group or together are a cyclic O-protecting group, $R^6$ is one of the groups:

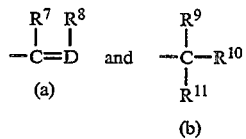

and A is the group:

(d)

wherein D is a methyne group or a nitrogen atom, $R^7$ is alkyl, aryl or arylalkyl and $R^8$ is hydrogen, alkyl, aryl or arylalkyl or $R^7$ and $R^8$ together with the two atoms to which they are attached is aryl, heteroaryl, cycloalkenyl or heterocycloalkenyl, $R^9$ is hydrogen and $R^{10}$ and $R^{11}$ taken together with the carbon atom to which they are attached, are cycloalkyl or heterocycloalkyl, Y is the bivalent residue of optionally N- and α-methylated phenylalanine, cyclohexalanine, tyrosine, O-methyltyrosine, α-napththylalanine or homophenylalanine linked with Z at the N-terminal, Z is acyl, in the form of an optically pure diastereomer, a diastereomeric racemate, or mixtures thereof as well as pharmaceutically usable salts thereof and a therapeutically inert excipient.

16. A composition in accordance with claim 15, wherein $R^2$ signifies imidazol-4-yl, $R^4$ and $R^5$ each independently signify hydrogen, alkanoyl, which is optionally mono- or multiply-substituted by carboxy, alkoxy or hydroxy, or an O-protecting group or together signify a cyclic O-protecting group.

17. A composition in accordance with claim 16, wherein $R^2$ signifies imidazol-4-yl, $R^4$ and $R^5$ each signify hydrogen, $R^7$ and $R^8$ each independently signify alkyl, aryl or arylalkyl or, together with the two atoms to which they are attached, aryl, heteroaryl, cycloalkenyl or heterocycloalkenyl.

18. A composition in accordance with claim 15, wherein $R^1$ signifies hydrogen, $R^2$ signifies imidazol-4-yl, $R^3$ signifies cyclohexylethyl, $R^4$ and $R^5$ each independently signify hydrogen or alkanoyl, which is optionally mono-substituted by dialkylamino, carboxy or alkoxy, or together signify a cyclic O-protecting group, D signifies a methyne group, $R^7$ signifies alkyl and $R^8$ signifies hydrogen or alkyl or $R^7$ and $R^8$ together with the two atoms to which they are attached signify aryl, heteroaryl or cycloalkenyl, Y signifies the bivalent residue of phenylalanine linked with Z at the N-terminal and Z signifies acyl.

19. A composition in accordance with claim 18, wherein $R^2$ signifies imidazol-4-yl, $R^4$ and $R^5$ each independently signify hydrogen or alkanoyl, which is optionally mono-substituted by methoxy, or together signify the acetal of pivalic aldehyde, $R^6$ signifies the group (b), $R^9$ signifies hydrogen, and $R^{10}$ and $R^{11}$ taken together with the carbon atom to which they are attached, signify cycloalkyl.

20. A composition in accordance with claim 19, wherein $R^2$ signifies imidazol-4-yl, $R^4$ and $R^5$ each signify hydrogen and $R^{10}$ and $R^{11}$ taken together with the carbon atom to which they are attached, signify cyclopropyl or cyclobutyl.

21. A pharmaceutical composition comprising an amount effective for the control of high blood pressure and cardiac insufficiency of a compound of the formula

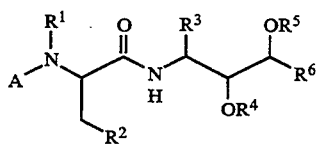

wherein $R^1$ signifies hydrogen or methyl, $R^2$ signifies imidazol-4-yl, $R^3$ signifies isobutyl, cyclohexylmethyl or benzyl, $R^4$ and $R^5$ each independently signify hydrogen, alkanoyl, which is optionally mono- or multiply-substituted by amino, monoalkylamino, dialkylamino, alkanoylamino, alkanoyloxyamino, carboxy, alkoxy or hydroxy, or an O-protecting group or together signify a cyclic O-protecting group, $R^6$ signifies one of the groups

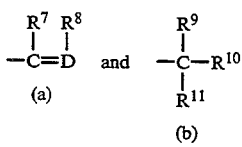

and A signifies the group

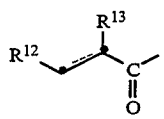

wherein D signifies a methyne group or a nitrogen atom, $R^7$ signifies alkyl, aryl or arylalkyl and $R^8$ signifies hydrogen, alkyl, aryl or aryialkyl or $R^7$ and $R^8$ together with the two atoms to which they are attached signify aryl, heteroaryl, cycloalkenyl or heterocycloalkenyl, $R^9$ signifies hydrogen or alkyl and $R^{10}$ and $R^{11}$ each independently signify alkyl, aryl, arylalkyl, cycloalkyl or the group

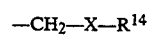

or, together with the carbon atom to which they are attached, cycloalkyl or heterocycloalkyl, with the proviso that, where $R^9$ signifies alkyl, $R^{10}$ and $R^{11}$ also signify alkyl, the dotted line can signify an additional bond, $R^{12}$ signifies phenyl, substituted phenyl, benzyl or naphthyl and $R^{13}$ signifies alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, alkylthioalkyl, alkylsulphinylalkyl or alkylsulphonylalkyl, X signifies an oxygen or sulphur atom or the group —NH— and $R^{14}$ signifies hydrogen, alkyl, cycloalkyl, arylalkyl, cycloalkylalkyl, alkylcarbonyl, arylcarbonyl or arylalkylcarbonyl, in the form of an optically pure diastereomer, a diastereomeric racemate, or mixtures thereof as well as pharmaceutically usable salts thereof, and a therapeutically inert excipient.

22. A composition in accordance with claim 21, wherein $R^2$ signifies imidazol-4-yl, $R^4$ and $R^5$ each independently signify hydrogen, alkanoyl, which is optionally mono- or multiply-substituted by carboxy, alkoxy or hydroxy, or an O-protecting group or together signify a cyclic O-protecting group and $R^{12}$ signifies phenyl, substituted phenyl or naphthyl.

23. A composition in accordance with claim 21, wherein $R^2$ signifies imidazol-4-yl, $R^4$ and $R^5$ each signify hydrogen, $R^7$ and $R^8$ each independently signify alkyl, aryl or arylalkyl or, together with the two atoms to which they are attached, aryl, heteroaryl, cycloalkenyl or heterocycloalkenyl and $R^{14}$ signifies alkyl, cycloalkyl, arylalkyl, cycloalkylalkyl, alkylcarbonyl, arylcarbonyl or arylalkylcarbonyl.

24. A composition in accordance with claim 21, wherein $R^1$ signifies hydrogen, $R^2$ signifies imidazol-4-yl, $R^3$ signifies cyclohexylmethyl, $R^4$ and $R^5$ each independently signify hydrogen or alkanoyl, which is optionally mono-substituted by dialkylamino, carboxy or alkoxy, or together mono-substituted by dialkylamino, carboxy or alkoxy, or together signify a cyclic O-protecting group, D signifies a methyne group, $R^7$ signifies alkyl and $R^8$ signifies hydrogen or alkyl or $R^7$ and $R^8$ together with the group (e) or, together with the carbon atoms to which they are attached, cycloalkyl or heterocycloalkyl, $R^{13}$ signifies alkylcarbonylalkyl, heterocycloalkylcarbonylalkyl, alkylsulphinylalkyl or alkylsulphonylalkyl, X signifies an oxygen atom and $R^{14}$ signifies hydrogen or arylalkyl.

25. A composition in accordance with claim 24, wherein $R^{13}$ signifies alkylcarbonylalkyl, heterocycloalkylcarbonylalkyl or alkylsulphonylalkyl.

26. A composition in accordance with claim 25, wherein $R^2$ signifies imidazol-4-yl $R^4$ and $R^5$ each independently signify hydrogen or alkanoyl, which is optionally mono-substituted by methoxy, or together signify the acetal of pivalic aldehyde, $R^6$ signifies the group (b), $R^9$ signifies hydrogen, $R^{10}$ and $R^{11}$ each independently signify alkyl or, together with the carbon atom to which they are attached, cycloalkyl, $R^{12}$ signifies phenyl or substituted phenyl, and $R^{13}$ signifies alkylcarbonylalkyl or alkylsulphonylalkyl.

27. A composition in accordance with claim 26, wherein $R^2$ signifies imidazol-4-yl, $R^4$ and $R^5$ each signify hydrogen, $R^{10}$ and $R^{11}$ taken together with the carbon atom to which they are attached signify cyclopropyl or cyclobutyl, $R^{12}$ signifies phenyl and $R^{13}$ signifies $C_1$-$C_4$-alkylcarbonylmethyl or $C_1$-$C_4$-alkyl-sulphonylmethyl.

28. A composition in accordance with claim 21, wherein the compound of formula I is selected from the group consisting of (S)—N—[(1S, 2R, 3RS)-1-(Cyclohexylmethyl)-4-ethyl-2,3-dihydroxyhexyl]-α-[(R)-α-(3,3-dimethyl-2-oxobutyl)hydrocinnamamido]imidazole-4-propionamide, (S)—N—[(1S, 2R, 3S)-3-cyclohexyl-1-(cyclohexylmethyl)-2,3-dihydroxy-propyl]-α-[(R)-α-(3,3-dimethyl-2-oxobutyl)hydrocinnamamaido] imidazole-4-propionamide, (S)—N—[(1S, 2R, 3S)-1-(cyclohexylmethyl)-2,3-dihydroxy-4-methylpentyl]-α-[(R)-α-(3,3-dimethyl-2-oxobutyl)hydrocinnamamido]imidazo-4-propionamide, (S)-α-[(S)-α-[(t-butylsulphonyl)-methyl]hydrocinnamamido]—N—[(1S, 2R, 3S)-1-(cyclohexylmethyl)-2,3-dihydroxy-3-phenyl-propyl]imidazole-4-propionamide, (S)-α-[(S)-α-[(t-butylsulphonyl)methyl]hydrocinnamamido]—N—[(1S, 2R, 3R)-1-(cyclohexylmethyl)-2,3-dihydroxy-3-phenylpropyl]imidazole-4-propionamide, (S)-α[(S)-α-[(t-butylsulphonyl)methyl]hydrocinnamamido]—N—[(1S, 2R, 3RS)-1-(cyclohexylmethyl)-2,3-dihydroxy-4,4-dimethylpentyl]imidazole-4-propionamide, (S)-α-[(S)-α-[(t-butylsulphonyl) methyl[hydrocinnamamido]—N—[(1S, 2R, 3S)-1-(cyclohexylmethyl)-2,3-dihydroxy-4-methylpentyl]imidazole-4-propionamide and (S)-α-[(S)-α-[(t-butylsulphonyl)methyl]hydrocinnamamido]—N—(1S, 2R, 3S)-3-cyclohexyl-1-(cyclohexylmethyl)-2,3-dihydroxypropyl]-imidazole-4-propionamide.

29. A composition in accordance with the claim 21, wherein the compound of formula I is selected from the group consisting of (S)-α[(S)-α-[(t-Butylsulphonyl)methyl]hydrocinnamamido] —N—[(1S, 2R, 3RS)-1-(cyclohexylmethyl)-2,3-dihydroxy-3-(2-furyl)propyl]imidazole-4-propionamide, (S)—N—[(1S, 2R, 3R or S)-1-(cyclohexylmethyl)-2,3-dihydroxy-3-[(R or S)-tetrahydro-2-furyl]propyl]-α-[(R)-α-(3,3-dimethyl-2-oxobutyl)hydrocinnamamido]imidazole-4-propionamide and (S)-α-[[(S)-α-[(t-butylsulphonyl)methyl]hydrocinnamamido]—N—[(1 S, 2R, 3R or S,Z)1-(cyclohexylmethyl)-2,3-dihydroxy-4-methyl-4-hexenyl]imidazole-4-propionamide.

30. A composition in accordance with claim 21, wherein the compound of formula I is selected from the group consisting of (S)-α-[(S)-α-[(t-butylsulphonyl)methyl]-1-naphthalenepropionamido]—N—[(1S, 2R, 3S)-1-(cyclohexylmethyl)-3-cyclopropyl-2,3-dihydroxypropyl]imidazole-4-propionamide, [(S)-α-[(S)-2-[(t-butylsulphonyl)methyl]-4-phenylbutyramido]—N—[(1S, 2R, 3S)-1-(cyclohexylmethyl)-3-cyclopropyl-2,3-dihydroxypropyl]imidazole-4-propionamide, (S)-α-[(R)-α[(t-butylsulphonyl)methyl[hydrocinnamamido]—N—[(1S, 2R, 3S)-1-(cyclohexylmethyl)-3-cyclopropyl-2,3-dihydroxypropyl]imidazole-4-propionamide and (S)—N—[(S)-1-[(2R or S, 4R, 5S)-2-t-butyl-5-isopropyl-1,2-dioxolan-4-yl]-2-cyclohexylethyl]-α-[(S)-α-[(t-butylsulphonyl)methyl]-hydrocinnamamido]imidazole-4-propionamide.

* * * * *